United States Patent
Katsuda et al.

(10) Patent No.: US 9,681,929 B2
(45) Date of Patent: Jun. 20, 2017

(54) DENTAL TREATING APPARATUS

(71) Applicant: J. Morita Manufacturing Corporation, Kyoto (JP)

(72) Inventors: Naoki Katsuda, Kyoto (JP); Seiichiro Yamashita, Kyoto (JP); Tomoaki Ueda, Kyoto (JP); Hideo Hijikata, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 89 days.

(21) Appl. No.: 14/485,471

(22) Filed: Sep. 12, 2014

(65) Prior Publication Data

US 2015/0086941 A1   Mar. 26, 2015

(30) Foreign Application Priority Data

Sep. 20, 2013   (JP) ................. 2013-195623

(51) Int. Cl.
*A61C 1/00*   (2006.01)
*A61C 5/02*   (2006.01)
(Continued)

(52) U.S. Cl.
CPC .............. *A61C 5/023* (2013.01); *A61C 1/186* (2013.01); *A61C 5/40* (2017.02); *A61C 5/44* (2017.02);
(Continued)

(58) Field of Classification Search
CPC ........... A61C 5/023; A61C 1/186; A61C 5/02; A61C 5/025
See application file for complete search history.

(56) References Cited

U.S. PATENT DOCUMENTS

| 4,473,329 A | 9/1984 | Aoshima et al. |
| 5,980,248 A | 11/1999 | Kusakabe et al. |

(Continued)

FOREIGN PATENT DOCUMENTS

| EP | 2567671 A1 | 3/2013 |
| JP | S5775712 A | 5/1982 |

(Continued)

OTHER PUBLICATIONS

Extended European Search Report issued in corresponding European Patent Application No. 14003022.2 dated Feb. 17, 2015 (7 pages).

(Continued)

*Primary Examiner* — Robert N Wieland
(74) *Attorney, Agent, or Firm* — Osha Liang LLP

(57) ABSTRACT

A dental treating apparatus according to the present invention includes: a hand piece; a head unit; a driving unit; a resistor for load detection; a load comparing unit; and a control unit. The hand piece drivably holds a cutting tool on the head unit. The driving unit drives the cutting tool in a normal rotation direction or in a reverse rotation direction. The resistor for load detection detects a load applied to the cutting tool. The load comparing unit compares the detected load and a reference load each time driving for rotating the cutting tool in the reverse rotation direction by a predetermined rotation angle is performed. The control unit controls the driving unit based on a result of comparison by the load comparing unit.

18 Claims, 13 Drawing Sheets

(51) Int. Cl.
*A61C 19/04* (2006.01)
*A61C 1/18* (2006.01)
*A61C 5/40* (2017.01)
*A61C 5/44* (2017.01)
*A61C 5/48* (2017.01)

(52) U.S. Cl.
CPC .............. *A61C 5/48* (2017.02); *A61C 19/041* (2013.01); *A61C 1/003* (2013.01); *A61C 1/0023* (2013.01)

(56) References Cited

U.S. PATENT DOCUMENTS

| | | | | |
|---|---|---|---|---|
| 2002/0064756 A1* | 5/2002 | Pagnini | ................... | A61C 5/02 433/102 |
| 2002/0182564 A1 | 12/2002 | Katsuda et al. | | |
| 2005/0042572 A1 | 2/2005 | Katsuda et al. | | |
| 2013/0224677 A1 | 8/2013 | Yamashita et al. | | |
| 2015/0342702 A1* | 12/2015 | Borgschulte | ............. | A61C 5/02 433/27 |

FOREIGN PATENT DOCUMENTS

| | | |
|---|---|---|
| JP | H0938108 A | 2/1997 |
| JP | 3264607 B2 | 3/2002 |
| JP | 2003-504113 A | 2/2003 |
| JP | 3615209 B2 | 2/2005 |
| JP | 2005-144194 A | 6/2005 |
| JP | 3676753 B2 | 7/2005 |
| JP | 2013-172840 A | 9/2013 |
| WO | 01/03601 A1 | 1/2001 |
| WO | 2010/066337 A1 | 6/2010 |
| WO | 2013/152346 A1 | 10/2013 |

OTHER PUBLICATIONS

Office Action in counterpart Japanese Patent Application No. 2013-195623 issued on Dec. 20, 2016 (19 pages).

* cited by examiner

FIG.12

|  | NORMAL ROTATION | | REVERSE ROTATION | |
|---|---|---|---|---|
|  | ROTATION ANGLE | NUMBER OF ROTATIONS (ROTATION ANGULAR SPEED) | ROTATION ANGLE | NUMBER OF ROTATIONS (ROTATION ANGULAR SPEED) |
| SETTING 1 | SMALLER | — | — | — |
| SETTING 2 | — | SMALLER | — | — |
| SETTING 3 | SMALLER | SMALLER | — | — |
| SETTING 4 | — | — | LARGER | — |
| SETTING 5 | — | — | — | LARGER |
| SETTING 6 | — | — | LARGER | LARGER |
| SETTING 7 | SMALLER | — | LARGER | — |
| SETTING 8 | SMALLER | — | — | LARGER |
| SETTING 9 | SMALLER | — | LARGER | LARGER |
| SETTING 10 | — | SMALLER | LARGER | — |
| SETTING 11 | — | SMALLER | — | LARGER |
| SETTING 12 | — | SMALLER | LARGER | LARGER |
| SETTING 13 | SMALLER | SMALLER | LARGER | — |
| SETTING 14 | SMALLER | SMALLER | — | LARGER |
| SETTING 15 | SMALLER | SMALLER | LARGER | LARGER |

FIG.13

|  | ROTATION ANGLE | NUMBER OF ROTATIONS (ROTATION ANGULAR SPEED) |
|---|---|---|
| SETTING A | NORMAL ROTATION < REVERSE ROTATION | — |
| SETTING B | — | NORMAL ROTATION < REVERSE ROTATION |
| SETTING C | NORMAL ROTATION < REVERSE ROTATION | NORMAL ROTATION < REVERSE ROTATION |

DENTAL TREATING APPARATUS

BACKGROUND OF THE INVENTION

Field of the Invention

The present invention relates to a dental treating apparatus with a hand piece, and more specifically to a dental treating apparatus that causes a cutting tool for cutting and enlarging an inner wall of a root canal of a tooth to be driven.

Description of the Background Art

In dental treatment, a root canal of a tooth is cut and enlarged for treatment in some cases. For this treatment, a dental treating apparatus having a cutting tool (referred to as "file or reamer") attached to a head unit of a hand piece is used and the cutting tool is driven to cut and enlarge the root canal of the tooth. Japanese Patent No. 3264607, Japanese Patent No. 3615209 and Japanese Patent No. 3676753 disclose various types of driving control in order to, for example, prevent breakage due to a load applied to the cutting tool when the dental treating apparatus causes the cutting tool to be driven to cut and enlarge the root canal of the tooth.

A dental treating apparatus disclosed in Japanese Patent No. 3264607 includes detecting means for detecting a load applied to a cutting tool, and control means for reversely rotating a cutting tool driving motor when the detected load reaches a preset reference.

A dental treating apparatus disclosed in Japanese Patent No. 3615209 includes driving means for driving a cutting tool, load detecting means for detecting a load applied to the cutting tool, root canal length measuring means for measuring a root canal length by using the cutting tool, reference load setting means for arbitrarily presetting a reference load, and control means for controlling the driving means. When the load detected by the load detecting means exceeds the reference load, the control means controls the driving means by any one of the operations of stopping driving of the cutting tool, reducing an amount of driving, reversing rotation, and repeating normal rotation and reverse rotation, such that the load applied to the cutting tool is reduced. Furthermore, based on a value of the root canal length measured by the root canal length measuring means, the control means controls the driving means such that the amount of driving the cutting tool becomes smaller as a distance from the cutting tool to a root apex becomes shorter.

A dental treating apparatus disclosed in Japanese Patent No. 3676753 includes driving means for driving a cutting tool, root canal length measuring means for measuring a root canal length, and control means for controlling the driving means such that the driving force of the cutting tool changes in accordance with a value of the root canal length measured by the root canal length measuring means. The control means includes number-of-rotations control means for controlling the number of rotations of the cutting tool. Based on the value of the root canal length measured by the root canal length measuring means, the number-of-rotations control means controls the driving means such that the number of rotations of the cutting tool becomes smaller as a distance from the cutting tool to a root apex becomes shorter.

In a dental treating apparatus disclosed in Japanese National Patent Publication. No. 2003-504113, a cutting tool is rotated clockwise or counterclockwise by a desired first rotation angle, and then, is rotated by a second rotation angle in a direction opposite to the first rotation angle. In order to discharge a cut piece from a root canal, the cutting tool is driven such that the first rotation angle is larger than the second rotation angle.

The cutting tool for cutting and enlarging the root canal of the tooth cuts into the root canal wall and contributes to cutting of the tooth when rotated clockwise, for example, whereas the cutting tool does not cut into the root canal wall and does not contribute to cutting of the tooth when rotated counterclockwise. For example, in the dental treating apparatus disclosed in Japanese National Patent Publication No. 2003-504113, twist driving is performed in which driving for rotating the cutting tool clockwise by a desired first rotation angle and then rotating the cutting tool counterclockwise by a second rotation angle is repeated. Therefore, when the cutting tool is rotated clockwise, the cutting tool cuts into the root canal wall and the load is applied to the cutting tool. On the other hand, when the cutting tool is rotated counterclockwise, cutting into the root canal wall is lessened and the applied load is also reduced.

However, if cutting into the root canal wall is not sufficiently lessened and the applied load is not sufficiently reduced when the cutting tool is rotated counterclockwise, the cutting tool further cuts into the root canal wall and more load is applied to the cutting tool when the cutting tool is rotated clockwise again, as compared with when the cutting tool is first rotated clockwise. Namely, in the dental treating apparatus disclosed in Japanese National Patent Publication No. 2003-504113, if the load applied to the cutting tool is not sufficiently reduced when the cutting tool is rotated counterclockwise, the excessive load is applied to the cutting tool when the cutting tool is rotated clockwise again, which resulted in breakage of the cutting tool.

In addition, in the dental treating apparatus disclosed in Japanese National Patent Publication No. 2003-504113, the cutting tool is rotated clockwise or counterclockwise by the desired first rotation angle, and then, is rotated by the second rotation angle in the direction opposite to the first rotation angle, and thus, the rotation that does not contribute to cutting of the tooth is inevitably included, which resulted in a decrease in tooth cutting efficiency.

SUMMARY OF THE INVENTION

The present invention provides a dental treating apparatus that can efficiently cut a tooth while preventing breakage of a cutting tool due to an applied load.

A dental treating apparatus according to the present invention includes: a hand piece; a driving unit; a load detecting unit; a load comparing unit; and a control unit. The hand piece drivably holds a cutting tool on a head unit. The driving unit drives the cutting tool, assuming that a normal rotation is a rotation in a direction in which the cutting tool cuts an object to be cut and a reverse rotation is a rotation in an opposite direction of the normal rotation. The load detecting unit detects a load applied to the cutting tool. The load comparing unit compares the load detected by the load detecting unit and a reverse rotation reference load. The control unit controls the driving unit based on a result of comparison by the load comparing unit, each time the driving unit performs driving for rotating the cutting tool in a reverse rotation direction.

In the dental treating apparatus according to the present invention, the control unit controls the driving unit based on the result of comparison by the load comparing unit, each time the driving unit performs the driving for rotating the cutting tool in the reverse rotation direction. Therefore, the driving of the cutting tool can be controlled after it is checked whether the load applied to the cutting tool has been sufficiently reduced or not. Thus, breakage of the cutting tool due to the applied load can be prevented.

In addition, in the dental treating apparatus according to the present invention, each time the driving unit performs the driving for rotating the cutting tool in the reverse rotation direction, it is checked whether the load applied to the cutting tool has been sufficiently reduced or not and the cutting tool is driven. Therefore, control is executed to prevent the cutting tool from being rotated in the reverse rotation direction excessively than necessary. Thus, the driving in the reverse rotation direction that does not contribute to cutting of the tooth can be reduced and the tooth can be efficiently cut.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 12 is a diagram showing combinations of parameters changed in accordance with a load applied to the cutting tool.

FIG. 13 is a diagram showing relation between the parameters changed in accordance with the load applied to the cutting tool.

DESCRIPTION OF THE PREFERRED EMBODIMENTS

Hereinafter, embodiments of the present invention are described with reference to the drawings.

First Embodiment

A dental treating apparatus according to a first embodiment of the present invention is a root canal treating device including a root canal enlarging and root canal length measuring system into which a dental hand piece for treatment on a root canal is incorporated. The dental treating apparatus according to the present invention is, however, not limited to the root canal treating device, and can be applied to a dental treating apparatus with a similar configuration.

Figure 1:
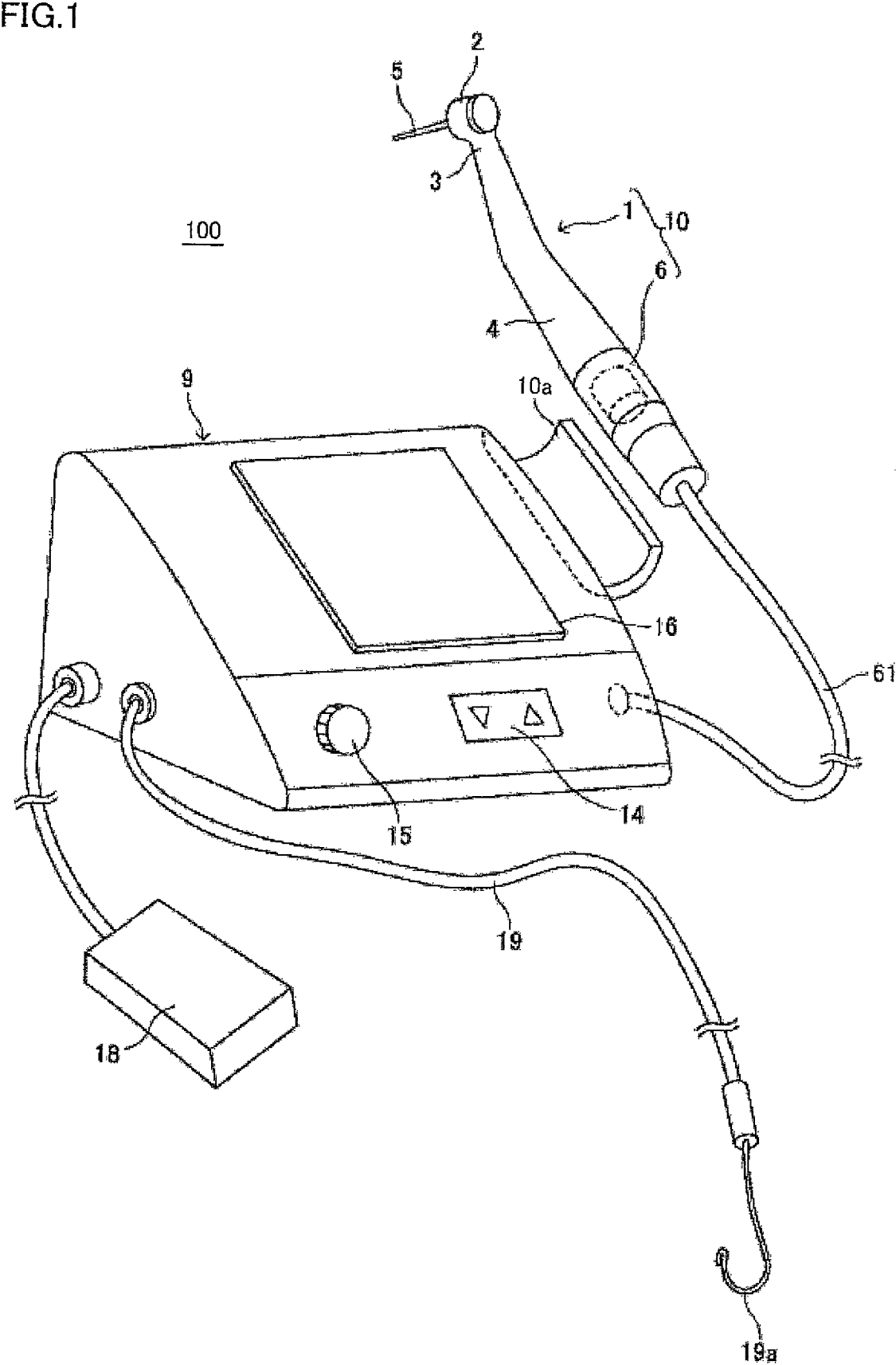
FIG. 1 is a schematic diagram showing an appearance of a configuration of a root canal treating device according to a first embodiment of the present invention.
Figure 2:
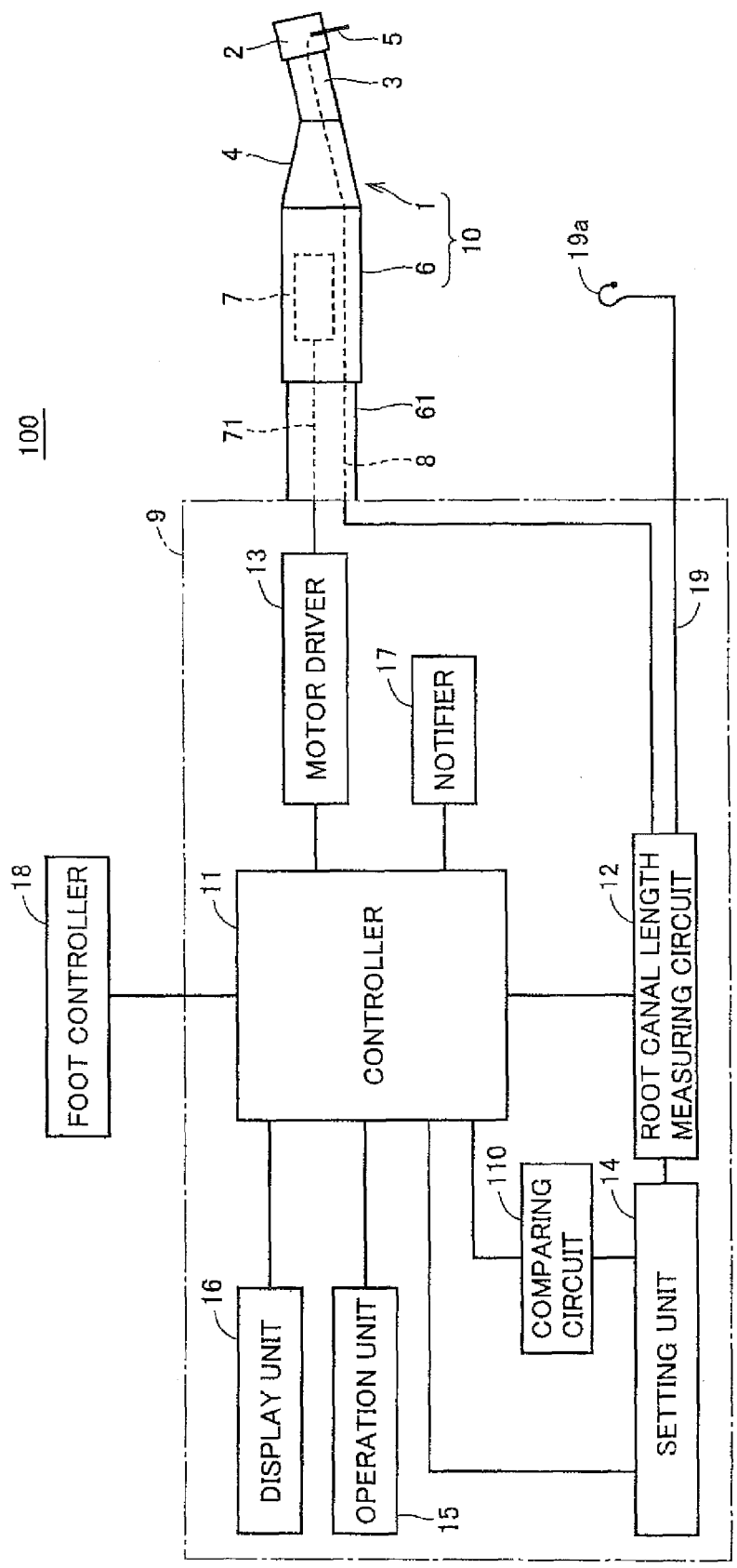
FIG. 2 is a block diagram showing a configuration of functions of the root canal treating device according to the first embodiment of the present invention.

FIG. 1 is a schematic diagram showing an appearance of a configuration of the root canal treating device according to the first embodiment of the present invention. FIG. 2 is a block diagram showing a configuration of functions of the root canal treating device according to the first embodiment of the present invention. A root canal treating device 100 as shown in FIG. 1 includes a hand piece 1 for treating dental root canal, a motor unit 6 and a control box 9.

Hand piece 1 for treating the dental root canal includes a head unit 2, a neck unit 3 with a small diameter connected to head unit 2, and a grip 4 connected to neck unit 3 and gripped by a hand or fingers. Further, to a base unit of grip 4, motor unit 6 is detachably connected for rotating and driving a cutting tool 5 (such as a file or a reamer) to be held on head unit 2. A dental instrument 10 is configured with hand piece 1 and motor unit 6 coupled to each other.

As shown in FIG. 2, a micro motor 7 is embedded in motor unit 6 that is connected to control box 9 through a hose 61 containing therein a power supply lead 71 for supplying power to micro motor 7, a signal lead 8 for transmitting a signal to a root canal length measuring circuit 12 to be described below, and the like. Here, signal lead 8 is a part of a conductive body for transmitting an electric signal, signal lead 8 being electrically connected to cutting tool 5 through motor unit 6 and hand piece 1. It is also noted that cutting tool 5 is one of electrodes of root canal length measuring circuit 12.

Control box 9 includes a controller 11, a comparing circuit 110, root canal length measuring circuit 12, a motor driver 13, a setting unit 14, an operation unit 15, a display unit 16, a notifier 17, and the like. As shown in FIG. 1, it should be noted that control box 9 is provided with a holder 10a holding instrument 10 when instrument 10 is not used, at a lateral part of a body. Also, a foot controller 18 is connected to controller 11 in control box 9. Further, a lead 19 is connected to root canal length measuring circuit 12 in control box 9. Although lead 19 is drawn out from control box 9, lead 19 may be drawn out to be bifurcated at an intermediate portion of hose 61. A mouth electrode 19a hung on a lip of a patient is attached to a tip end of lead 19 in an electrically conductive state. It should be noted that mouth electrode 19a is the other one of the electrodes of root canal length measuring circuit 12.

A primary part of controller 11 for controlling the whole system for enlarging the root canal and measuring the root canal length is configured by a microcomputer. Comparing circuit 110, root canal length measuring circuit 12, motor driver 13, setting unit 14, operation unit 15, display unit 16, notifier 17, and foot controller 18 are connected to controller 11. Assuming that a rotation direction in which cutting tool 5 cuts an object to be cut is a normal rotation and a rotation direction opposite to the normal rotation is a reverse rotation, controller 11 can perform normal driving in which control is executed to perform driving for rotating cutting tool 5 in the normal rotation direction, reverse driving in which control is executed to perform driving for rotating cutting tool 5 in the reverse rotation direction, and twist driving in which control is executed to perform driving for rotating cutting tool 5 by repeating the normal rotation and the reverse rotation. Controller 11 can change parameters such as a rotation angle and a rotation angular speed (number of rotations) in the normal rotation as well as a rotation angle and a rotation angular speed in the reverse rotation, and control driving for rotating cutting tool 5.

The rotation angular speed herein refers to an amount indicating the speed of rotation of cutting tool 5, and by dividing the rotation angular speed by 2π radian, the number of rotations is obtained. In the following embodiments, the speed of rotation of cutting tool 5 is indicated by using the number of rotations, instead of using the rotation angular speed. Revolutions per minute (rpm) is used as a unit of the number of rotations.

Each time the driving for rotating cutting tool 5 in the reverse rotation direction by a predetermined rotation angle (hereinafter, also simply referred to as "predetermined reverse rotation angle") is performed, comparing circuit 110 compares a load applied to cutting tool 5 and a reverse rotation reference load. Namely, in comparing circuit 110, an interval of comparing the load applied to cutting tool 5 and the reverse rotation reference load is set as every time cutting tool 5 is rotated in the reverse rotation direction by the predetermined rotation angle. Assuming that the predetermined reverse rotation angle is, for example, 40 degrees in the case of performing the twist driving for rotating cutting tool 5 in the normal rotation direction by 160 degrees and in the reverse rotation direction by 40 degrees, comparing circuit 110 compares the load applied to cutting tool 5 and the reverse rotation reference load three times, each time cutting tool 5 makes one rotation. Although the interval of performing load comparison in comparing circuit 110 is set by the reverse rotation angle, the present invention is not limited thereto. The interval may be set by the reverse rotation driving period and the like. If the number of rotations and the number of reverse rotations of cutting tool 5 are fixed, setting the interval by the reverse rotation driving period means the same thing as setting the interval by the reverse rotation angle. When the number of rotations and the number of reverse rotations of cutting tool 5 are, for example, 120 rpm, rotating cutting tool 5 in the normal rotation direction by 160 degrees and in the reverse rotation direction by 40 degrees means the same thing as driving cutting tool 5 for about 0.278 seconds.

Root canal length measuring circuit 12 configures a closed circuit with cutting tool 5 inserted in the root canal of the tooth as one electrode and mouth electrode 19*a* hung on the lip of the patient as the other electrode. Root canal length measuring circuit 12 can measure a distance from an apical position of the tooth to a tip end of cutting tool 5 by applying voltage between cutting tool 5 and mouth electrode 19*a* and measuring impedance between cutting tool 5 and mouth electrode 19*a*. An amount of insertion of the cutting tool, that is, a distance from an opening of the root canal to the tip end of the cutting tool, when root canal length measuring circuit 12 detects that the tip end of cutting tool 5 has reached the apical position can be defined as the root canal length. It should be noted that a method for electrically measuring the root canal length by measuring the impedance between cutting tool 5 and mouth electrode 19*a* is publicly known and all publicly-known methods for electrically measuring the root canal length can be applied to root canal treating device 100 according to the first embodiment of the present invention.

Motor driver 13 is connected to micro motor 7 via power supply lead 71 and controls the power supplied to micro motor 7 based on a control signal from controller 11. Motor driver 13 can control the rotation direction, the number of rotations, the rotation angle and the like of micro motor 7, namely the rotation direction, the number of rotations, the rotation angle and the like of cutting tool 5 by controlling the power supplied to micro motor 7.

Setting unit 14 sets a reference for controlling the rotation direction, the number of rotations, the rotation angle and the like of cutting tool 5. Setting unit 14 can also set the reverse rotation reference load compared with the load applied to cutting tool 5 in comparing circuit 110, and the reverse rotation angle indicating the interval of comparison, and can set the apical position or a position located at a prescribed distance from the apical position as a reference position in advance by using root canal length measuring circuit 12. Since the reference position is set in setting unit 14 in advance, root canal treating device 100 can change the parameters such as the rotation direction, the number of rotations and the rotation angle of cutting tool 5 when the tip end of cutting tool 5 reaches this reference position. In addition to the reverse rotation reference load, setting unit 14 may also set reference values of the load (e.g., values for determining the manner of gradual change of the load (reverse rotation reference load>load C>load B>load A)).

In addition to setting the parameters such as the number of rotations and the rotation angle of cutting tool 5, operation unit 15 can also select whether to perform root canal length measurement or not. Operation unit 15 can also manually switch between the normal rotation driving and the reverse rotation driving as well as between the normal rotation driving and the twist driving.

Display unit 16 displays a position of the tip end of cutting tool 5 in the root canal and the rotation direction, the number of rotations, the rotation angle and the like of cutting tool 5 as described below. Also, display unit 16 can display information for notifier 17 to notify a user.

Notifier 17 notifies the user by light, sound, vibration, and the like of the driving state of cutting tool 5 that is being executed by controller 11. Specifically, notifier 17 includes an LED (Light Emitting Diode), a speaker, an oscillator, and the like according to the need to notify the user of the driving state of cutting tool 5, and colors of the light emitted from the LED change or sounds outputted from the speaker change based on whether the driving in the normal rotation direction is being executed or the driving in the reverse rotation direction is being executed. Also, notifier 17 need not include the LED, the speaker, the oscillator and the like separately if display unit 16 can display the driving state of cutting tool 5 for the user.

Foot controller 18 is an operation unit for performing driving control on cutting tool 5 by micro motor 7 by a stepping operation. It should be noted that the driving control on cutting tool 5 by micro motor 7 is not limited to foot controller 18, namely, an operation switch (not shown) is provided in grip 4 of hand piece 1 to perform the driving control on cutting tool 5 by this operation switch and foot controller 18. Also, for example, in a state where the stepping operation via foot controller 18 is performed, and further when root canal length measuring circuit 12 detects that cutting tool 5 has been inserted into the root canal, the rotation of cutting tool 5 may be started.

It should be noted that a configuration is disclosed in that control box 9 of root canal treating device 100 is put on a tray table or a side table installed on a lateral part of a dental treatment table and used. The present invention is, however, not limited to such a configuration but can include a configuration in that control box 9 is incorporated into the tray table or the side table.

Figure 3:
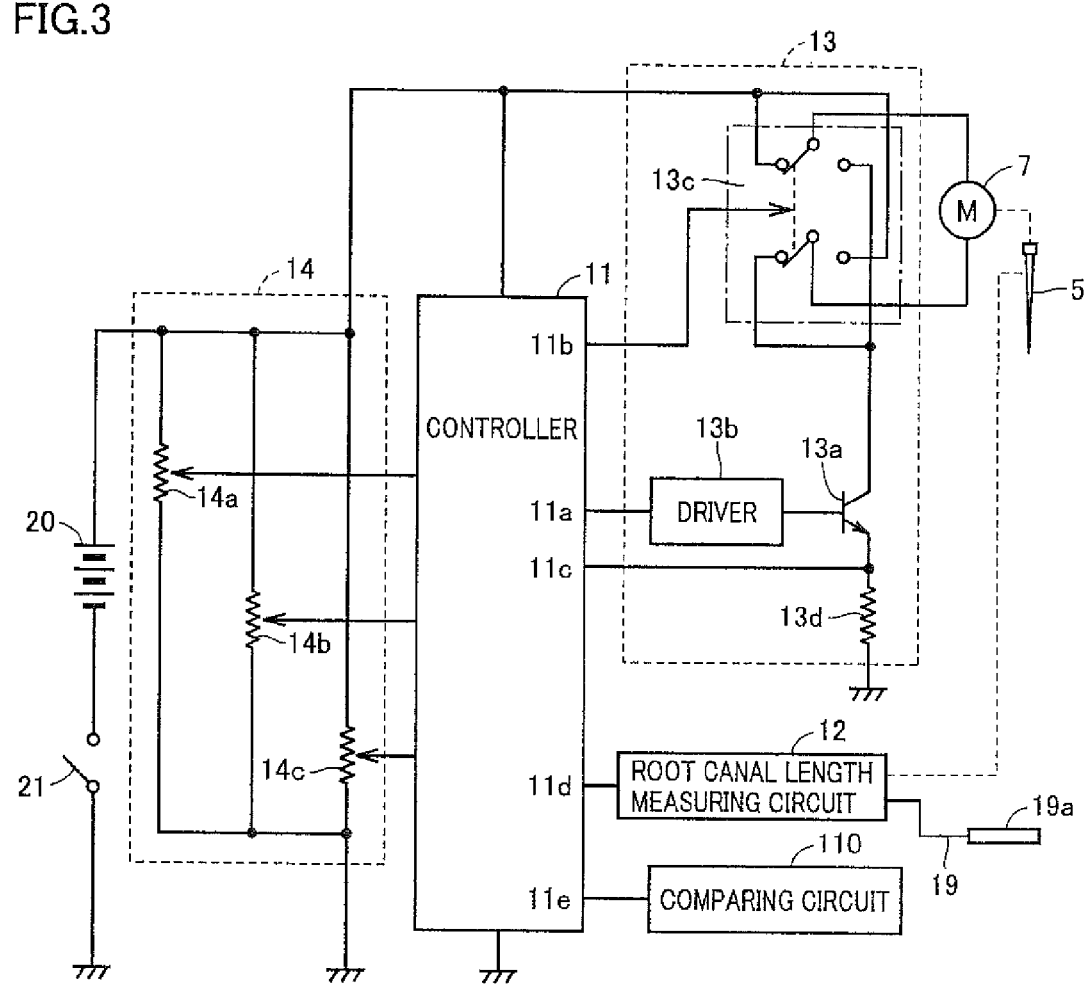
FIG. 3 is a circuit diagram showing a circuit configuration of the root canal treating device according to the first embodiment of the present invention.

Next, a circuit configuration of root canal treating device 100 for performing the driving control on cutting tool 5 is described in more detail. FIG. 3 is a circuit diagram showing a circuit configuration of root canal treating device 100 according to the first embodiment of the present invention. In root canal treating device 100 shown in FIG. 3, components of micro motor 7, controller 11, root canal length measuring circuit 12, motor driver 13, and setting unit 14 that are involved in the driving control on cutting tool 5 are illustrated.

Furthermore, motor driver 13 includes a transistor switch 13a, a transistor driver circuit 13b, a rotation direction switching switch 13c, and a resistor 13d for load detection. Setting unit 14 includes a variable resistor 14a for setting the reference load (normal rotation reference load and reverse rotation reference load), a variable resistor 14b for setting a duty, and a variable resistor 14c for setting the reference position. Although setting unit 14 includes a configuration for setting the reverse rotation angle indicating the interval of comparing the detected load and the reverse rotation reference load in comparing circuit 110, or the like, this configuration is not shown in FIG. 3. A main power supply 20 and a main switch 21 are also connected to root canal treating device 100 shown in FIG. 3. Cutting tool 5 is held on micro motor 7 via an appropriate gear mechanism and the like, although not shown.

Transistor driver circuit 13h operates in response to a control signal outputted from a port 11a of controller 11, and controls ON/OFF of transistor switch 13a and drives micro motor 7. Micro motor 7 rotates in the normal rotation direction or in the reverse rotation direction in accordance with a state of rotation direction switching switch 13c. When the control signal outputted from port 11a of controller 11 has, for example, a pulse waveform repeated in a certain cycle, a width of the pulse waveform, that is, a duty ratio is adjusted by variable resistor 14b for setting a duty in setting unit 14. Micro motor 7 drives cutting tool 5 at the number of rotations corresponding to this duty ratio.

In response to a control signal outputted from a port 11b of controller 11, rotation direction switching switch 13c switches between driving cutting tool 5 in the normal rotation direction and driving cutting tool 5 in the reverse rotation direction. At a port 11c, controller 11 receives an amount of current (or voltage value) at a terminal of resistor 13d for load detection and detects a load applied to cutting tool 5. Therefore, resistor 13d for load detection functions as a load detecting unit for detecting the load applied to cutting tool 5. It should be noted that the load detecting unit is not limited to the configuration for detecting the load applied to cutting tool 5 based on the amount of current (or voltage value) at the terminal of resistor 13d for load detection. The load detecting unit may have another configuration such as a configuration for detecting the load applied to cutting tool 5 by using a torque sensor provided, for example, at a driving portion of cutting tool 5. The detected load is converted in controller 11 into, for example, a torque value applied to cutting tool 5, and is displayed on display unit 16. Comparing circuit 110 converts the voltage value at the terminal of resistor 13d for load detection into a torque value, and compares the torque value and a value set by variable resistor 14a for setting the reference load. As a matter of course, comparing circuit 110 may be configured to compare the load applied to cutting tool 5 and the reference load, without conversion into the torque value.

Furthermore, controller 11 receives the root canal length measured by root canal length measuring circuit 12 at a port 11d. Therefore, root canal length measuring circuit 12 functions as a driving state detecting unit for detecting a position of the tip end of cutting tool 5 in the root canal. Controller 11 also outputs, from a port 11e to comparing circuit 110, the load applied to cutting tool 5 which has been detected by resistor 13d for load detection, and receives, from port 11e, a comparison result obtained by comparison with the reference load by comparing circuit 110. Therefore, comparing circuit 110 functions as a load comparing unit for comparing the load detected by the load detecting unit and the reference load.

Figure 4:
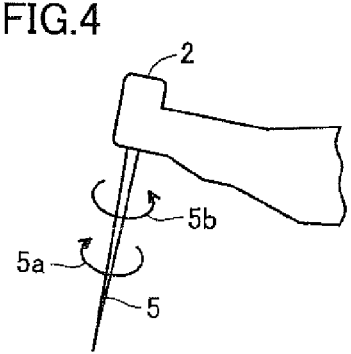
FIG. 4 is a schematic diagram showing a rotation direction of a cutting tool in the case of twist driving.

FIG. 4 is a schematic diagram showing the rotation direction of cutting tool 5. FIG. 4 shows driving in the normal rotation 5a direction for rotating cutting tool 5 clockwise as directed toward the tip end of cutting tool 5, and driving in the reverse rotation 5b direction for rotating cutting tool 5 counterclockwise. It should be noted that twist driving is driving for alternately performing the driving in the normal rotation 5a direction and the driving in the reverse rotation 5b direction.

Figure 5:
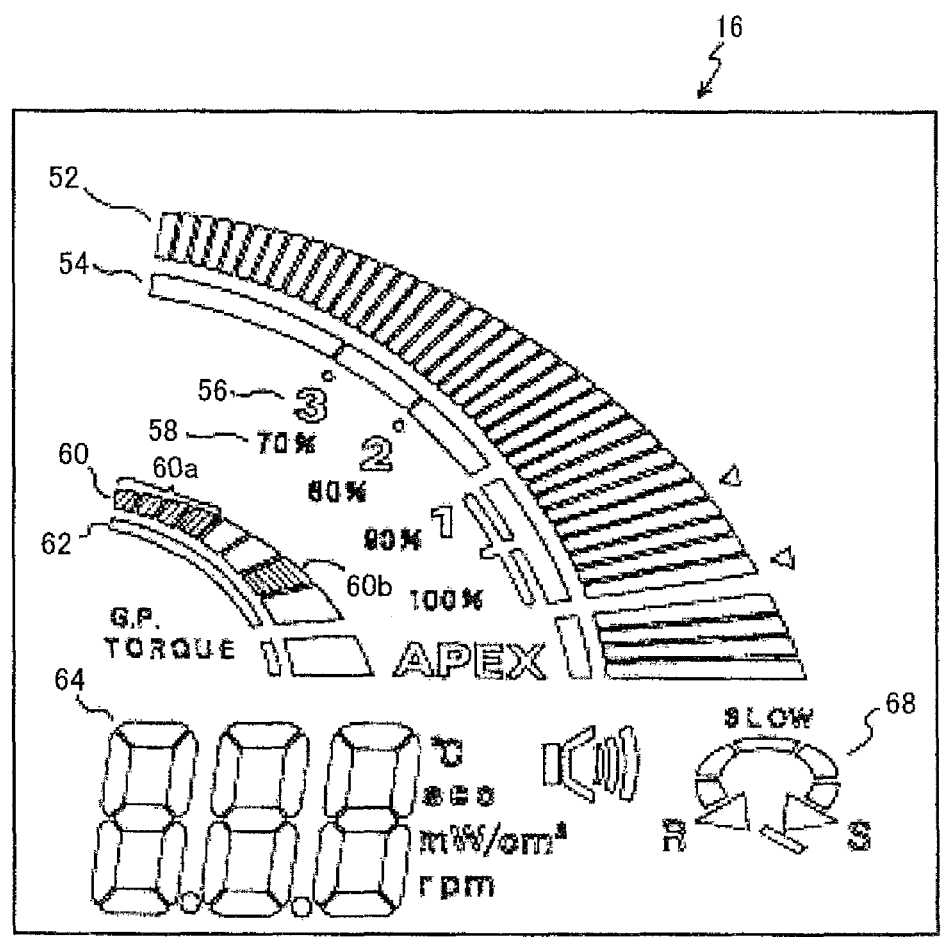
FIG. 5 is a diagram showing a display example of a liquid crystal display panel of a display unit shown in FIG. 1.

Next, display of a liquid crystal display panel of display unit 16 shown in FIG. 1 is described. FIG. 5 is a diagram showing a display example of the liquid crystal display panel of display unit 16 shown in FIG. 1.

Display unit 16 shown in FIG. 5 is the liquid crystal display panel, and is provided with a dot display unit 52 including many elements for displaying the measured root canal length in detail, a zone display unit 54 for dividing the root canal length into a plurality of zones and displaying the root canal length in a stepwise manner, a boundary display unit 56 for displaying a boundary of each zone, and an arrival rate display unit 58 for displaying a rate of arrival at the root apex.

Dot display unit 52 is configured such that the elements are sequentially displayed from the top to the bottom as the tip end of cutting tool 5 comes closer to the root apex. A position of the gauge "APEX" shows a position of the root apex, and arrival of the elements at this gauge means that the tip end of cutting tool 5 has nearly arrived at the position of the root apex.

Display unit 16 is also provided with a dot display unit 60 including many elements for displaying the load detected by resistor 13d for load detection (refer to FIG. 3), and a zone display unit 62 for dividing the load into a plurality of zones and displaying the load in a stepwise manner. Dot display unit 60 is configured such that the elements are sequentially displayed from the top to the bottom as the load detected by resistor 13d for load detection becomes larger.

For example, the load applied to cutting tool 5 when cutting tool 5 is cutting the tooth is displayed on dot display unit 60 by diagonally shaded elements 60a. In order to prevent frequent switching of displays, dot display unit 60 may have a peak hold function to display, for a certain time period, a maximum value of the load detected within a prescribed time period.

An element 60b corresponding to the reference load set by variable resistor 14a for setting the reference load (refer to FIG. 3) may also be displayed on dot display unit 60. By displaying element 60b on dot display unit 60, it is possible to visualize how much margin is present in the load detected by resistor 13*d* for load detection with respect to the reference load.

Display unit 16 is further provided with a numerical value display unit 64 for numerically displaying the number of rotations of cutting tool 5 and the load applied to cutting tool 5, and a rotation display unit 68 for displaying the orientation of rotation of cutting tool 5 (normal rotation, reverse rotation) and the number of rotations of cutting tool 5.

Next, driving of cutting tool 5 of root canal treating device 100 according to the first embodiment will be described. In root canal treating device 100 according to the first embodiment, each time the driving for rotating cutting tool 5 in the reverse rotation direction by the predetermined rotation angle is performed, comparing circuit 110 compares the load detected by resistor 13*d* for load detection and the reverse rotation reference load. Root canal treating device 100 according to the first embodiment sets a rotation angle in the normal rotation direction (hereinafter, also simply referred to as "normal rotation angle") at 160 degrees and a rotation angle in the reverse rotation direction (hereinafter, also simply referred to as "reverse rotation angle") at 40 degrees and performs the twist driving of cutting tool 5. Root canal treating device 100 according to the first embodiment is not, however, limited thereto. For example, when the tip end of cutting tool 5 reaches a prescribed position in the root canal and cutting tool 5 is driven in the reverse rotation direction, the detected load and the reverse rotation reference load may be compared. Namely, it is possible to apply such a configuration that the detected load and the reverse rotation reference load are compared when cutting tool 5 is driven in the reverse rotation direction based on some kind of condition.

Figure 6:
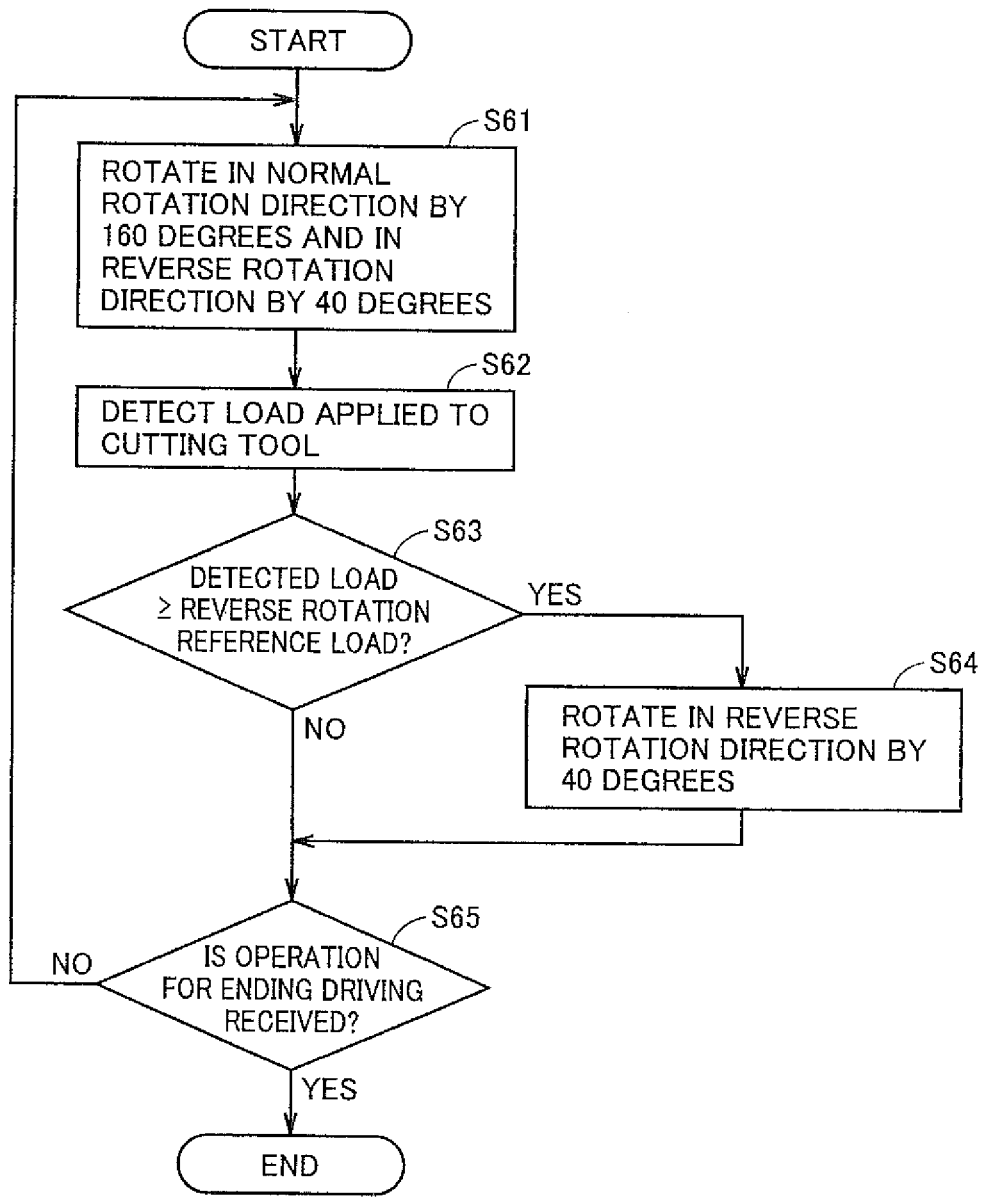
FIG. 6 is a flowchart for describing one example of driving of the cutting tool of the root canal treating device according to the first embodiment of the present invention.

FIG. 6 is a flowchart for describing one example of driving of cutting tool 5 of root canal treating device 100 according to the first embodiment of the present invention. First, controller 11 executes control to perform the twist driving for rotating cutting tool 5 in the normal rotation direction by 160 degrees and thereafter in the reverse rotation direction by 40 degrees (step S61). Initial values set in controller 11 are used as the number of rotations in the normal rotation direction (hereinafter, also simply referred to as "the number of normal rotations") and the number of rotations in the reverse rotation direction (hereinafter, also simply referred to as "the number of reverse rotations"), and they are not changed in the process in the flowchart shown in FIG. 6.

Next, resistor 13*d* for load detection detects the load applied to cutting tool 5 when cutting tool 5 is rotated in the reverse rotation direction by 40 degrees (step S62). In the description of the configuration of root canal treating device 100 according to the first embodiment, resistor 13*d* for load detection detects the load applied to cutting tool 5 after cutting tool 5 is rotated in the reverse rotation direction by 40 degrees. The present invention is not, however, limited thereto. Resistor 13*d* for load detection may detect the load applied to cutting tool 5 at any point in time during rotation of cutting tool 5 in the reverse rotation direction by 40 degrees. Furthermore, a maximum value or an average value of the load or at least one of a plurality of load values detected by resistor 13*d* for load detection during rotation in the reverse rotation direction by 40 degrees (during rotation by the predetermined reverse rotation angle) may be used as the load applied to cutting tool 5. As a result, appropriate detection of the load applied to cutting tool 5, which is required to prevent breakage of the cutting tool, becomes possible.

Next, comparing circuit 110 compares the load detected by resistor 13*d* for load detection and the reverse rotation reference load set by variable resistor 14*a* for setting the reference load (reverse rotation reference load) in setting unit 14 (step S63). As a result, it is possible to detect cutting into the root canal wall by cutting tool 5, which is one cause of breakage of cutting tool 5. If the detected load is equal to or larger than the reverse rotation reference load (YES in step S63), controller 11 executes control to perform the driving for further rotating cutting tool 5 in the reverse rotation direction by 40 degrees (step S64). As a result, the load applied to cutting tool 5 can be further reduced.

In the description of the configuration of root canal treating device 100 according to the first embodiment, the load applied to cutting tool 5 is detected after cutting tool 5 is rotated in the reverse rotation direction by 40 degrees, and comparing circuit 110 compares the detected load and the reverse rotation reference load. The present invention is not, however, limited thereto. Root canal treating device 100 according to the first embodiment may be configured such that the load applied to cutting tool 5 is detected during rotation in the reverse rotation direction by 40 degrees (during rotation by the predetermined reverse rotation angle), and comparing circuit 110 compares the detected load and the reference load by the time cutting tool 5 finishes rotating in the reverse rotation direction by 40 degrees. As a result, in root canal treating device 100, the next driving can be performed based on the comparison result by comparing circuit 110, immediately after the driving for rotating cutting tool 5 in the reverse rotation direction by 40 degrees is performed. Therefore, cutting tool 5 can be driven efficiently.

Controller 11 also executes control to perform the driving for rotating cutting tool 5 in the normal rotation direction by 160 degrees and in the reverse rotation direction by 40 degrees. Namely, the rotation angle for rotating cutting tool 5 in the normal rotation direction is set to be larger than the reverse rotation angle for rotating cutting tool 5 in the reverse rotation direction. As a result, in root canal treating device 100, the rotation angle in the normal rotation direction that contributes to cutting of the tooth is set to be larger than the rotation angle in the reverse rotation direction that does not contribute to cutting of the tooth, and thus, the tooth cutting efficiency can be enhanced. In order to further reduce the load applied to cutting tool 5 at the expense of the tooth cutting efficiency, the reverse rotation angle for rotating cutting tool 5 in the reverse rotation direction may be brought closer to or may be set to be the same as the rotation angle for rotating cutting tool 5 in the normal rotation direction.

If the detected load is smaller than the reverse rotation reference load (NO in step S63), or after cutting tool 5 is rotated in the reverse rotation direction by 40 degrees, controller 11 determines whether the operation for ending the driving is received from operation unit 15 or not (step S65). If the operation for ending the driving is received from operation unit 15 (YES in step S65), controller 11 ends the driving. If the operation for ending the driving is not received from operation unit 15 (NO in step S65), the process returns to step S61 and controller 11 drives cutting tool 5 to be rotated in the normal rotation direction by 180 degrees. Controller 11 may be configured such that after cutting tool 5 is rotated in the reverse rotation direction by 40 degrees in step S64, the process returns to step S62, and if the detected load is equal to or larger than the reverse rotation reference load, cutting tool 5 is further rotated in the reverse rotation direction by 40 degrees.

Figure 7:
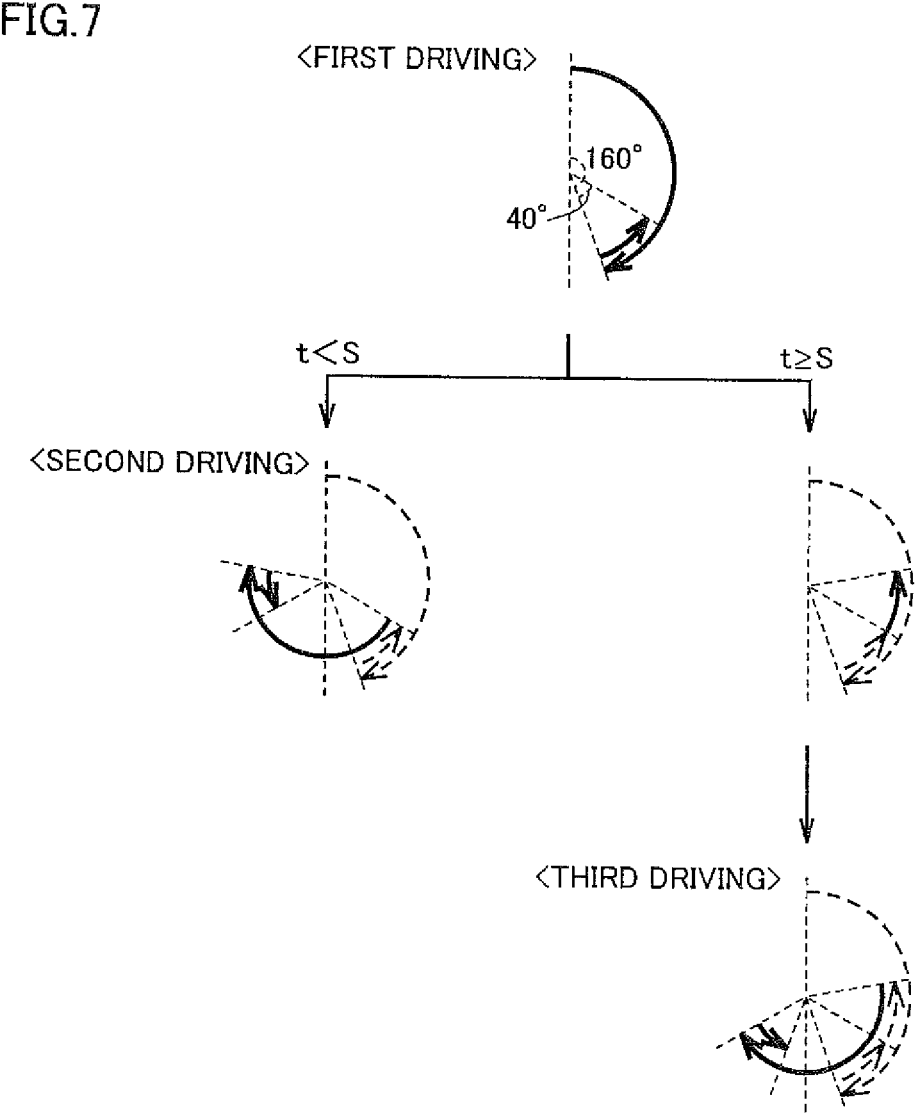
FIG. 7 is a schematic diagram for describing one example of driving of the cutting tool of the root canal treating device according to the first embodiment of the present invention.

Description will be given to how controller 11 drives cutting tool 5 as a result of the driving in accordance with the flowchart shown in FIG. 6. FIG. 7 is a schematic diagram for describing one example of driving of cutting tool 5 of root canal treating device 100 according to the first embodiment of the present invention. A clockwise arrow shown in FIG. 7 indicates that cutting tool 5 is driven in the normal rotation direction, and an angle formed by the clockwise arrow indicates a rotation angle for rotating cutting tool 5 in the normal rotation direction. On the other hand, a counterclockwise arrow indicates that cutting tool 5 is driven in the reverse rotation direction, and an angle formed by the counterclockwise arrow indicates a rotation angle for rotating cutting tool 5 in the reverse rotation direction. In the following description with reference to FIG. 7, driving until determination of whether to switch driving or not is made based on the comparison result by comparing circuit 110 is defined as one driving.

First, in the first driving, controller 11 executes control to perform the twist driving for rotating cutting tool 5 in the normal rotation direction by 160 degrees and thereafter in the reverse rotation direction by 40 degrees (corresponding to step S61 shown in FIG. 6). In accordance with a result of comparison between a detected load t and a reverse rotation reference load s by comparing circuit 110, the second driving has two types of drivings. Specifically, if detected load t is smaller than reverse rotation reference load s (t<s), controller 11 executes control to perform the twist driving for rotating cutting tool 5 in the normal rotation direction by 160 degrees and thereafter in the reverse rotation direction by 40 degrees (corresponding to step S61 shown in FIG. 6). As a result, controller 11 has controlled cutting tool 5 to perform the twist driving twice. On the other hand, if detected load t is equal to or larger than reverse rotation reference load s (t≥s), controller 11 executes control to perform the driving for rotating cutting tool 5 in the reverse rotation direction by 40 degrees (corresponding to step S64 shown in FIG. 6). As a result, controller 11 has executed control to perform the twist driving for rotating cutting tool 5 in the normal rotation direction by 160 degrees and in the reverse rotation direction by 80 degrees. Although controller 11 executes control to rotate cutting tool 5 in the reverse rotation direction and thereafter perform the twist driving, controller 11 may execute control to perform the driving for rotating cutting tool 5 in the reverse rotation direction by 40 degrees, until detected load t becomes smaller than reverse rotation reference load s.

In the third driving, different driving is performed in accordance with whether the twist driving of cutting tool 5 has been performed or cutting tool 5 has been driven in the reverse rotation direction in the second driving. First, when the twist driving of cutting tool 5 has been performed in the second driving, the process returns to the same situation as the first driving, and thus, the following description will not be repeated. On the other hand, when cutting tool 5 has been driven in the reverse rotation direction, controller 11 executes control to perform the twist driving for rotating cutting tool 5 in the normal rotation direction by 160 degrees and thereafter in the reverse rotation direction by 40 degrees (corresponding to step S61 shown in FIG. 6). In the third and subsequent drivings, the process returns to the same situation as the first driving, and thus, the following description will not be repeated.

As described above, in root canal treating device 100 according to the first embodiment of the present invention, each time the driving for rotating cutting tool 5 in the reverse rotation direction by the predetermined reverse rotation angle (e.g., 40 degrees) is performed, controller 11 executes control to perform the driving for rotating, in the reverse rotation direction, cutting tool 5 that is being controlled to perform the twist driving, when the load detected by resistor 13*d* for load detection is equal to or larger than the reverse rotation reference load. Therefore, in root canal treating device 100 according to the first embodiment, the driving in the normal rotation direction, of the twist driving, can be performed after it is checked whether the load applied to cutting tool 5 has been sufficiently reduced or not. Thus, breakage of the cutting tool due to the applied load can be prevented.

In root canal treating device 100 according to the first embodiment of the present invention, each time the driving for rotating cutting tool 5 in the reverse rotation direction by the predetermined reverse rotation angle (e.g., 40 degrees) is performed, motor driver 13 is controlled based on the result of comparison by resistor 13*d* for load detection. Root canal treating device 100 according to the first embodiment of the present invention is not, however, limited thereto. Each time the driving for rotating cutting tool 5 in the reverse rotation direction is performed, motor driver 13 may be controlled based on the result of comparison by resistor 13*d* for load detection.

In addition, in root canal treating device 100 according to the first embodiment, each time the driving for rotating cutting tool 5 in the reverse rotation direction by the predetermined reverse rotation angle is performed, it is checked whether the load applied to cutting tool 5 has been sufficiently reduced or not. Therefore, control is executed to prevent cutting tool 5 from being rotated in the reverse rotation direction excessively than necessary, and thus, the driving in the reverse rotation direction that does not contribute to cutting of the tooth is reduced and the tooth is efficiently cut.

In root canal treating device 100 according to the first embodiment, the twist driving for rotating cutting tool 5 in the normal rotation direction by 160 degrees and in the reverse rotation direction by 40 degrees is performed, and each time cutting tool 5 is rotated in the reverse rotation direction by 40 degrees (predetermined reverse rotation angle), the detected load and the reverse rotation reference load are compared. The present invention is not, however, limited thereto. For example, the twist driving for rotating cutting tool 5 in the normal rotation direction by 360 degrees or 720 degrees and in the reverse rotation direction by 120 degrees or 240 degrees may be performed, and each time cutting tool 5 is rotated in the reverse rotation direction by 120 degrees or 240 degrees (predetermined reverse rotation angle), the detected load and the reverse rotation reference load may be compared.

In the description of root canal treating device 100 according to the first embodiment, when the detected load is equal to or larger than the reverse rotation reference load as a result of comparison by comparing circuit 110, controller 11 executes control to perform the driving for rotating, in the reverse rotation direction, cutting tool 5 that is being controlled to perform the twist driving. Root canal treating device 100 according to the first embodiment is not, however, limited thereto. When the detected load is equal to or larger than the reverse rotation reference load as a result of comparison by comparing circuit 110, controller 11 may change the reverse rotation angle of cutting tool 5 that is being controlled to perform the twist driving to become larger and execute control to perform the driving for rotating cutting tool 5.

Second Embodiment

In the description of the configuration of root canal treating device 100 according to the first embodiment, each time cutting tool 5 is rotated in the reverse rotation direction by 40 degrees, the detected load and the reverse rotation reference load are compared. In accordance with a root canal treating device according to a second embodiment, such a configuration will be described that the detected load and the normal rotation reference load are compared each time the cutting tool is further rotated in the normal rotation direction by 160 degrees.

Since the root canal treating device according to the second embodiment has the same configuration as that of root canal treating device 100 according to the first embodiment shown in FIGS. 1 to 3, the same reference characters are used and detailed description will not be repeated.

Figure 8:
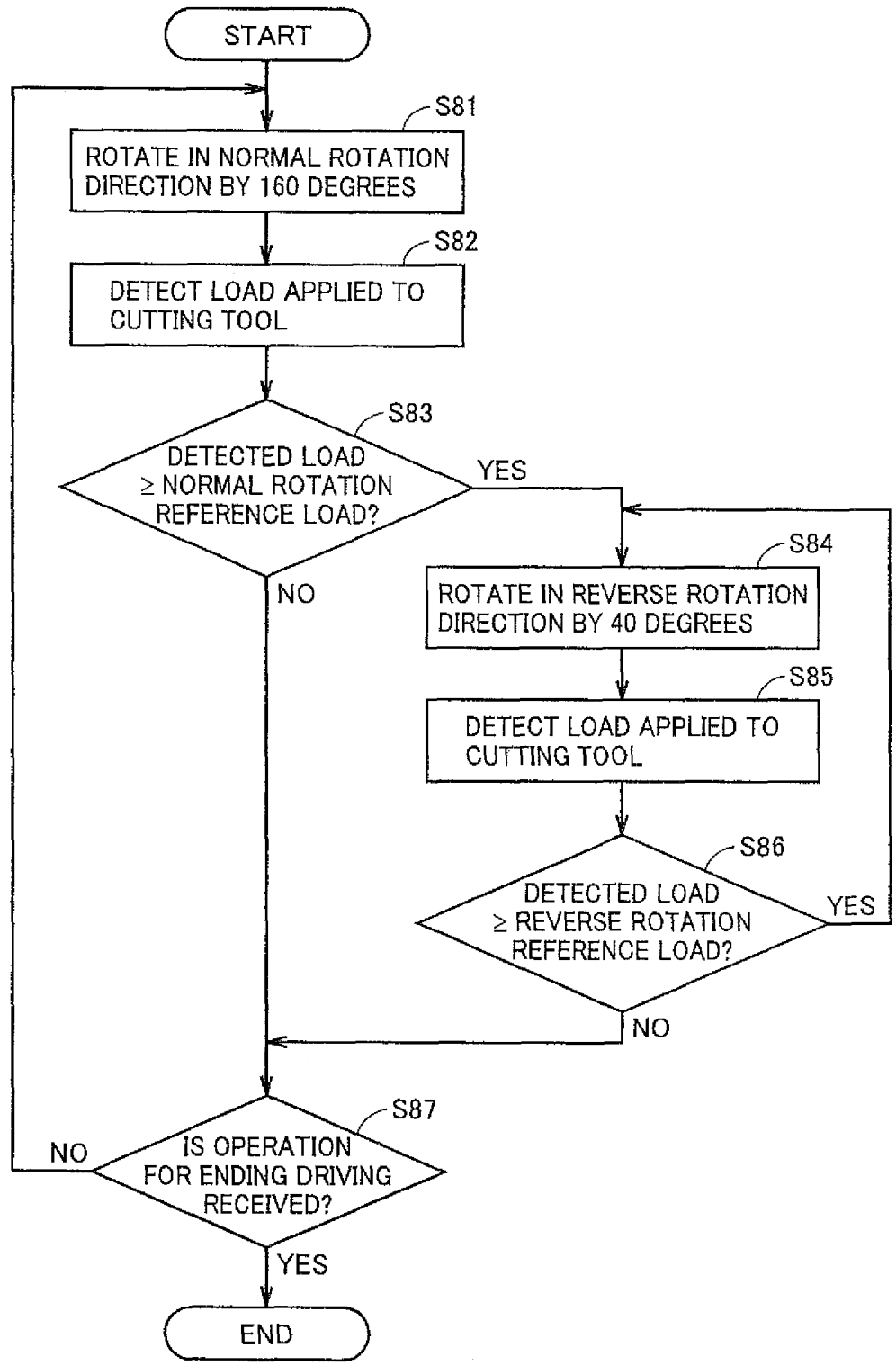
FIG. 8 is a flowchart for describing one example of driving of a cutting tool of a root canal treating device according to a second embodiment of the present invention.

FIG. 8 is a flowchart for describing one example of driving of cutting tool 5 of root canal treating device 100 according to the second embodiment of the present invention. Also in root canal treating device 100 according to the second embodiment of the present invention, control is executed to perform the twist driving for rotating cutting tool 5 in the normal rotation direction by 160 degrees and thereafter in the reverse rotation direction by 40 degrees. First, controller 11 executes control to perform the driving for rotating cutting tool 5 in the normal rotation direction by 160 degrees, of the twist driving (step S81). The initial values set in controller 11 are used as the number of normal rotations and the number of reverse rotations, and they are not changed in the process in the flowchart shown in FIG. 8.

Next, resistor 13d for load detection detects the load applied to cutting tool 5 when cutting tool 5 is rotated in the normal rotation direction by 160 degrees (step S82). In the description of the configuration of root canal treating device 100 according to the second embodiment, resistor 13d for load detection detects the load applied to cutting tool 5, after cutting tool 5 is rotated in the normal rotation direction by 160 degrees. The present invention is not, however, limited thereto. Resistor 13d for load detection may detect the load applied to cutting tool 5 at any point in time during rotation of cutting tool 5 in the normal rotation direction by 160 degrees. Furthermore, a maximum value or an average value of the load or at least one of a plurality of load values detected by resistor 13d for load detection during rotation by 160 degrees (during rotation by the predetermined rotation angle) may be used as the load applied to cutting tool 5.

Next, comparing circuit 110 compares the load detected by resistor 13d for load detection and the normal rotation reference load set by variable resistor 14a for setting the reference load (normal rotation reference load) in setting unit 14 (step S83). If the detected load is equal to or larger than the normal rotation reference load (YES in step S83), controller 11 executes control to perform the driving for rotating cutting tool 5 in the reverse rotation direction by 40 degrees (step S84). In the description of the configuration of root canal treating device 100 according to the second embodiment, the load applied to cutting tool 5 is detected after cutting tool 5 is rotated in the normal rotation direction by 160 degrees, and comparing circuit 110 compares the detected load and the normal rotation reference load. The present invention is not, however, limited thereto. Root canal treating device 100 according to the second embodiment may be configured such that the load applied to cutting tool 5 is detected during rotation by 160 degrees (during rotation by the predetermined normal rotation angle), and comparing circuit 110 compares the detected load and the normal rotation reference load by the time cutting tool 5 finishes rotating by 160 degrees.

Next, resistor 13d for load detection detects the load applied to cutting tool 5 when cutting tool 5 is rotated in the reverse rotation direction by 40 degrees (step S85). In the description of the configuration of root canal treating device 100 according to the second embodiment, resistor 13d for load detection detects the load applied to cutting tool 5, after cutting tool 5 is rotated in the reverse rotation direction by 40 degrees. The present invention is not, however, limited thereto. Resistor 13d for load detection may detect the load applied to cutting tool 5 at any point in time during rotation of cutting tool 5 in the reverse rotation direction by 40 degrees. Furthermore, a maximum value or an average value of the load or at least one of a plurality of load values detected by resistor 13d for load detection during rotation by 40 degrees (during rotation by the predetermined reverse rotation angle) may be used as the load applied to cutting tool 5.

Next, comparing circuit 110 compares the load detected by resistor 13d for load detection and the reverse rotation reference load set by variable resistor 14a for setting the reference load (reverse rotation reference load) in setting unit 14 (step S86). If the detected load is equal to or larger than the reverse rotation reference load (YES in step S86), the process returns to step S84 and controller 11 executes control to perform the driving for further rotating cutting tool 5 in the reverse rotation direction by 40 degrees. In the description of the configuration of root canal treating device 100 according to the second embodiment, the load applied to cutting tool 5 is detected after cutting tool 5 is rotated in the reverse rotation direction by 40 degrees, and comparing circuit 110 compares the detected load and the reverse rotation reference load. The present invention is not, however, limited thereto. Root canal treating device 100 according to the second embodiment may be configured such that the load applied to cutting tool 5 is detected during rotation in the reverse rotation direction by 40 degrees (during rotation by the predetermined reverse rotation angle), and comparing circuit 110 compares the detected load and the reverse rotation reference load by the time cutting tool 5 finishes rotating in the reverse rotation direction by 40 degrees. In addition, in root canal treating device 100 according to the second embodiment, the normal rotation reference load compared with the load detected in step S83 and the reverse rotation reference load compared with the load detected in step S86 may be set to have the same value or difference values. As a result, root canal treating device 100 according to the second embodiment can have a high degree of freedom for setting the reference load and can perform various drivings.

If the detected load is smaller than the normal rotation reference load or the reverse rotation reference load (NO in steps S83 and S86), controller 11 determines whether the operation for ending the driving is received from operation unit 15 or not (step S87). If the operation for ending the driving is received from operation unit 15 (YES in step S87), controller 11 ends the driving. If the operation for ending the driving is not received from operation unit 15 (NO in step S87), the process returns to step S81 and controller 11 drives cutting tool 5 to be rotated in the normal rotation direction by 160 degrees.

Figure 9:
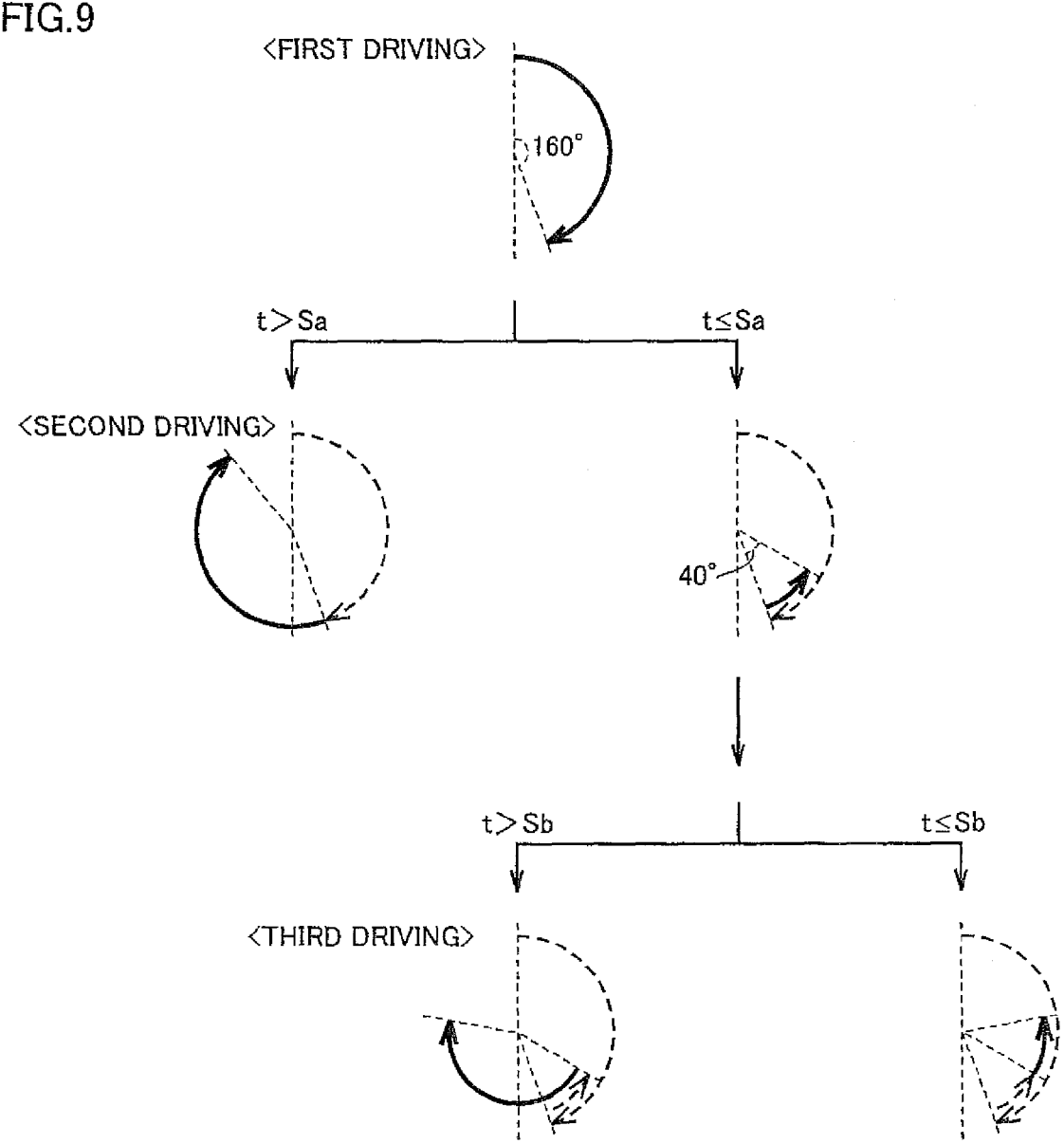
FIG. 9 is a schematic diagram for describing one example of driving of the cutting tool of the root canal treating device according to the second embodiment of the present invention.

Description will be given to how controller 11 drives cutting tool 5 as a result of the driving in accordance with the flowchart shown in FIG. 8. FIG. 9 is a schematic diagram for describing one example of driving of cutting tool 5 of root canal treating device 100 according to the second embodiment of the present invention. A clockwise arrow shown in FIG. 9 indicates that cutting tool 5 is driven in the normal rotation direction, and an angle formed by the clockwise arrow indicates a rotation angle for rotating cutting tool 5 in the normal rotation direction. On the other hand, a counterclockwise arrow indicates that cutting tool 5 is driven in the reverse rotation direction, and an angle formed by the counterclockwise arrow indicates a rotation angle for rotating cutting tool 5 in the reverse rotation direction. In the following description with reference to FIG. 9, driving until determination of whether to switch driving or not is made based on the comparison result by comparing circuit 110 is defined as one driving.

First, in the first driving, controller 11 drives cutting tool 5 to be rotated in the normal rotation direction by 160 degrees (corresponding to step S81 shown in FIG. 8). In accordance with a result of comparison between detected load t and a normal rotation reference load sa by comparing circuit 110, the second driving has two types of drivings. Specifically, if detected load t is smaller than normal rotation reference load sa (t<sa), controller 11 executes control to perform the driving for rotating cutting tool 5 in the normal rotation direction by 160 degrees (step S81 shown in FIG. 8). As a result, controller 11 continuously drives cutting tool 5 in the normal rotation direction, and the driving in the normal rotation direction that contributes to cutting of the tooth can be increased. On the other hand, if detected load t is equal to or larger than normal rotation reference load sa (t≥sa), controller 11 executes control to perform the driving for rotating cutting tool 5 in the reverse rotation direction by 40 degrees (corresponding to step S84 shown in FIG. 8). As a result, controller 11 executes control to perform the twist driving for rotating cutting tool 5 in the normal rotation direction by 160 degrees and in the reverse rotation direction by 40 degrees.

In the third driving, different driving is performed in accordance with whether cutting tool 5 has been driven in the normal rotation direction or cutting tool 5 has been driven in the reverse rotation direction in the second driving. First, when cutting tool 5 has been driven in the normal rotation direction in the second driving, the process returns to the same situation as the first driving, and thus, the following description will not be repeated.

When cutting tool 5 has been driven in the reverse rotation direction in the second driving, the third driving has two types of drivings in accordance with a result of comparison between detected load t and a reverse rotation reference load sb by comparing circuit 110. Specifically, if detected load t is smaller than reverse rotation reference load sb (t<sb), controller 11 executes control to perform the driving for rotating cutting tool 5 in the normal rotation direction by 160 degrees (corresponding to step S81 shown in FIG. 8). As a result, controller 11 executes control to perform the twist driving and thereafter executes control to perform the driving for rotating cutting tool 5 in the normal rotation direction by 160 degrees again. On the other hand, if detected load t is equal to or larger than reverse rotation reference load sb (t≥sb), controller 11 executes control to perform the driving for further rotating cutting tool 5 in the reverse rotation direction by 40 degrees (corresponding to step S84 shown in FIG. 8). As a result, controller 11 executes control to perform the twist driving and thereafter executes control to perform the driving for further rotating cutting tool 5 in the reverse rotation direction by 40 degrees. As a result, detected load t is equal to or larger than reverse rotation reference load sb, and thus, lessening of the cutting into the root canal wall is regarded as insufficient and cutting tool 5 is further rotated in the reverse rotation direction to sufficiently lessen the cutting into the root canal wall.

In the fourth driving, when cutting tool 5 has been driven in the normal rotation direction in the third driving, the process returns to the same situation as the first driving. When cutting tool 5 has been driven in the reverse rotation direction in the third driving, the process returns to the same situation as the driving for rotating cutting tool 5 in the reverse rotation direction in the second driving. Therefore, the following description will not be repeated.

As described above, in root canal treating device 100 according to the second embodiment, each time the driving for further rotating cutting tool 5 in the normal rotation direction by the predetermined normal rotation angle (e.g., 160 degrees) is performed, comparing circuit 110 compares the load detected by resistor 13d for load detection and the normal rotation reference load, and when the detected load is equal to or larger than the normal rotation reference load, controller 11 executes control to perform the driving for rotating cutting tool 5 in the reverse rotation direction. Therefore, in root canal treating device 100 according to the second embodiment, the driving can be controlled to rotate cutting tool 5 in the normal rotation direction after the load applied to cutting tool 5 is sufficiently reduced. Thus, breakage of the cutting tool due to the applied load can be prevented.

Third Embodiment

In accordance with a root canal treating device according to a third embodiment of the present invention, such a configuration will be described that at least one parameter of the rotation angle and the rotation angular speed in the normal rotation as well as the rotation angle and the rotation angular speed in the reverse rotation is changed in accordance with a result of comparison by the comparing circuit.

Figure 10:
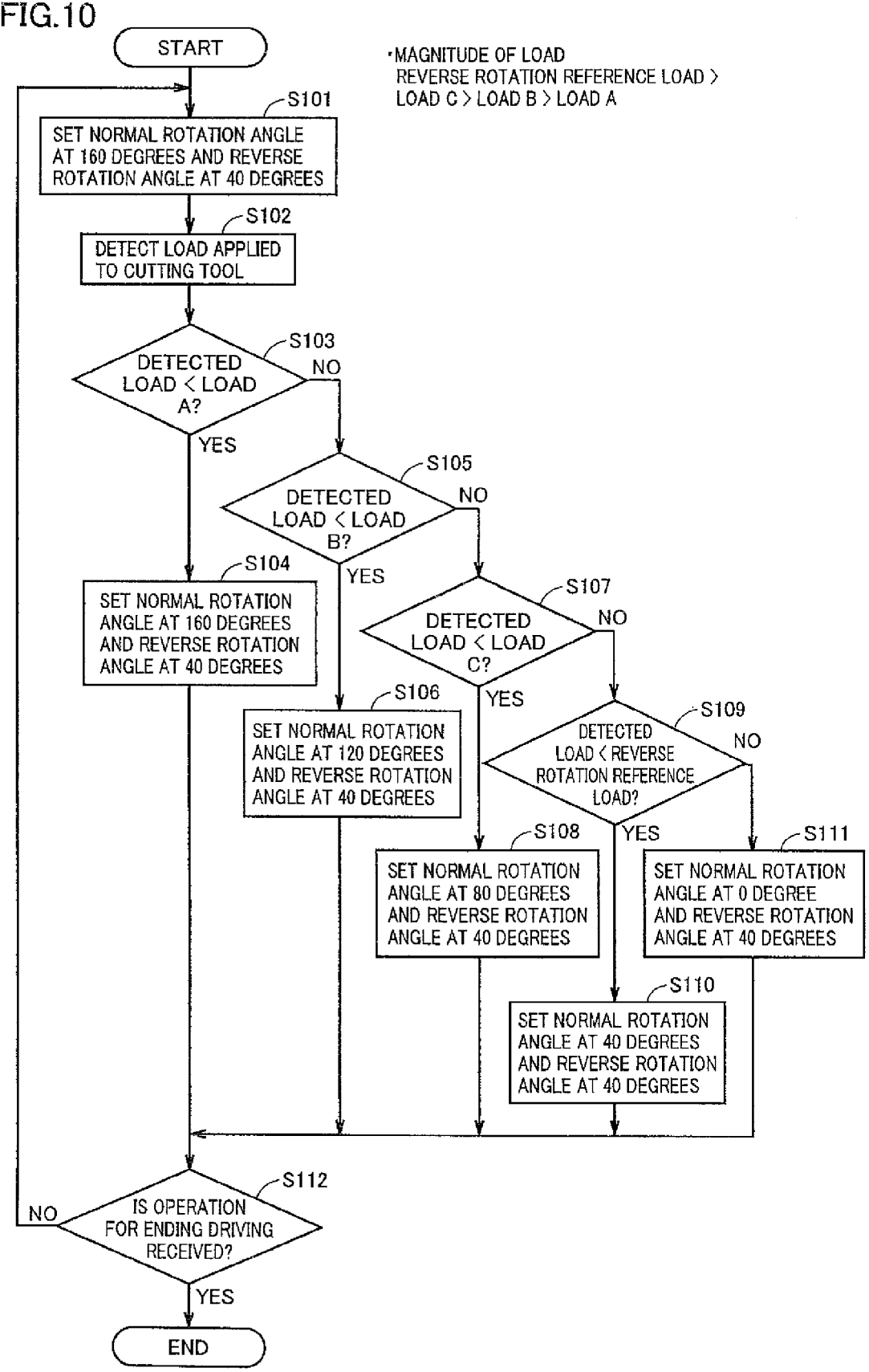
FIG. 10 is a flowchart for describing one example of driving of a cutting tool of a root canal treating device according to a third embodiment of the present invention.

FIG. 10 is a flowchart for describing one example of driving of cutting tool 5 of root canal treating device 100 according to the third embodiment of the present invention. First, controller 11 sets the normal rotation angle at 160 degrees and the reverse rotation angle at 40 degrees (initial values), and drives cutting tool 5 (step S101). The initial values (e.g., 120 rpm) set in controller 11 are used as the number of normal rotations and the number of reverse rotations, and they are not changed in the process in the flowchart shown in FIG. 10.

Next, resistor 13d for load detection detects the load applied to cutting tool 5 when cutting tool 5 is rotated in the reverse rotation direction by 40 degrees (step S102). In the description of the configuration of root canal treating device 100 according to the third embodiment, resistor 13d for load detection detects the load applied to cutting tool 5 after cutting tool 5 is rotated in the reverse rotation direction by 40 degrees. The present invention is not, however, limited thereto. Resistor 13d for load detection may detect the load applied to cutting tool 5 at any point in time during rotation of cutting tool 5 in the reverse rotation direction by 40 degrees. Furthermore, a maximum value or an average value of the load or at least one of a plurality of load values detected by resistor 13d for load detection during rotation in the reverse rotation direction by 40 degrees (during rotation by the predetermined reverse rotation angle) may be used as the load applied to cutting tool 5. As a result, appropriate detection of the load applied to cutting tool 5, which is required to prevent breakage of the cutting tool, becomes possible.

Next, comparing circuit 110 compares the load detected by resistor 13*d* for load detection and a load A set in setting unit 14 (step S103). If the detected load is smaller than load A (YES in step S103), controller 11 sets the normal rotation angle at 160 degrees and the reverse rotation angle at 40 degrees (initial values), and controls the driving of cutting tool 5 (step S104). Namely, controller 11 determines that the load applied to cutting tool 5 is not worth considering because the detected load is smaller than load A, and sets the normal rotation angle and the reverse rotation angle at the initial values and drives cutting tool 5. Also in the description of the configuration of root canal treating device 100 according to the third embodiment, the load applied to cutting tool 5 is detected after cutting tool 5 is rotated in the reverse rotation direction by 40 degrees, and comparing circuit 110 compares the detected load and the reverse rotation reference load. The present invention is not, however, limited thereto. Root canal treating device 100 according to the third embodiment may be configured such that the load applied to cutting tool 5 is detected during rotation in the reverse rotation direction by 40 degrees (during rotation by the predetermined reverse rotation angle), and comparing circuit 110 compares the detected load and the reference load by the time cutting tool 5 finishes rotating in the reverse rotation direction by 40 degrees. As a result, in root canal treating device 100, the next driving can be performed based on the comparison result by comparing circuit 110, immediately after the driving for rotating cutting tool 5 in the reverse rotation direction by 40 degrees is performed. Therefore, cutting tool 5 can be driven efficiently.

On the other hand, if the detected load is equal to or larger than load A (NO in step S103), comparing circuit 110 compares the load detected by resistor 13*d* for load detection and a load B (>load A) set in setting unit 14 (step S105). If the detected load is smaller than load B (YES in step S105), controller 11 sets the normal rotation angle at 120 degrees and the reverse rotation angle at 40 degrees, and controls the driving of cutting tool 5 (step S106). Namely, since the small load is applied to cutting tool 5 though the detected load is smaller than load B, controller 11 sets the normal rotation angle to become smaller than the initial value in consideration of the load applied to cutting tool 5, and controls the driving of cutting tool 5.

On the other hand, if the detected load is equal to or larger than load B (NO in step S105), comparing circuit 110 compares the load detected by resistor 13*d* for load detection and a load C (>load B) set in setting unit 14 (step S107). If the detected load is smaller than load C (YES in step S107), controller 11 sets the normal rotation angle at 80 degrees and the reverse rotation angle at 40 degrees, and controls the driving of cutting tool 5 (step S108). Namely, since the load equal to or larger than load B is applied to cutting tool 5 though the detected load is smaller than load C, controller 11 sets the normal rotation angle to become smaller than the value set in step S106, and controls the driving of cutting tool 5.

On the other hand, if the detected load is equal to or larger than load C (NO in step S107), comparing circuit 110 compares the load detected by resistor 13*d* for load detection and the reverse rotation reference load (>load C) set by variable resistor 14*a* for setting the reference load (reverse rotation reference load) in setting unit 14 (step S109). If the detected load is smaller than the reverse rotation reference load (YES in step S109), controller 11 sets the normal rotation angle at 40 degrees and the reverse rotation angle at 40 degrees, and controls the driving of cutting tool 5 (step S110). Namely, since the load equal to or larger than load C is applied to cutting tool 5 though the detected load is smaller than the reverse rotation reference load, controller 11 sets the normal rotation angle to become smaller than the value set in step S108, and controls the driving of cutting tool 5.

On the other hand, if the detected load is equal to or larger than the reverse rotation reference load (NO in step S109), controller 11 sets the normal rotation angle at 0 degree and the reverse rotation angle at 40 degrees, and controls the driving of cutting tool 5 (step S104). Namely, controller 11 executes control to perform the driving for further rotating cutting tool 5 in the reverse rotation direction by 40 degrees, similarly to the first embodiment.

Controller 11 controls the driving of cutting tool 5 in accordance with the normal rotation angles and the reverse rotation angles set in steps S104, S106, S108, S110, and S111, and thereafter, determines whether the operation for ending the driving is received from operation unit 15 or not (step S112). If the operation for ending the driving is received from operation unit 15 (YES in step S112), controller 11 ends the driving. If the operation for ending the driving is not received from operation unit 15 (NO in step S112), the process returns to step S102 and resistor 13*d* for load detection detects the load applied to cutting tool 5 when cutting tool 5 is rotated in the reverse rotation direction by 40 degrees.

Such an example of root canal treating device 100 has been described that in steps S101 to S111, the parameter of the normal rotation angle is gradually reduced and cutting tool 5 is driven, as the load applied to cutting tool 5 becomes larger in the order of load A, load B, load C, and the reverse rotation reference load. The present invention is not, however, limited thereto. In root canal treating device 100, the parameter of the normal rotation angle may be continuously changed in accordance with the load applied to cutting tool 5. For example, controller 11 continuously changes the parameter of the normal rotation angle from 160 degrees to 0 degree in accordance with the change of the load applied to cutting tool 5 from load A to the reverse rotation reference load. Furthermore, in root canal treating device 100, the parameter of the reverse rotation angle may also be changed in accordance with the load applied to cutting tool 5. At this time, the predetermined reverse rotation angle, which is a timing at which resistor 13*d* for load detection detects the load applied to cutting tool 5, is also changed in accordance with the change of the parameter of the reverse rotation angle. An upper limit value of each of the normal rotation angle and the reverse rotation angle is not limited to 160 degrees. The rotation angle may be set to be equal to or larger than 160 degrees and the reference load may be set in accordance with the rotation angle.

The flowchart shown in FIG. 10 describes the example in which controller 11 changes the parameter of the rotation angle in accordance with the load applied to cutting tool 5. Controller 11 may change the parameter of the number of rotations in accordance with the load applied to cutting tool 5.

Figure 11:
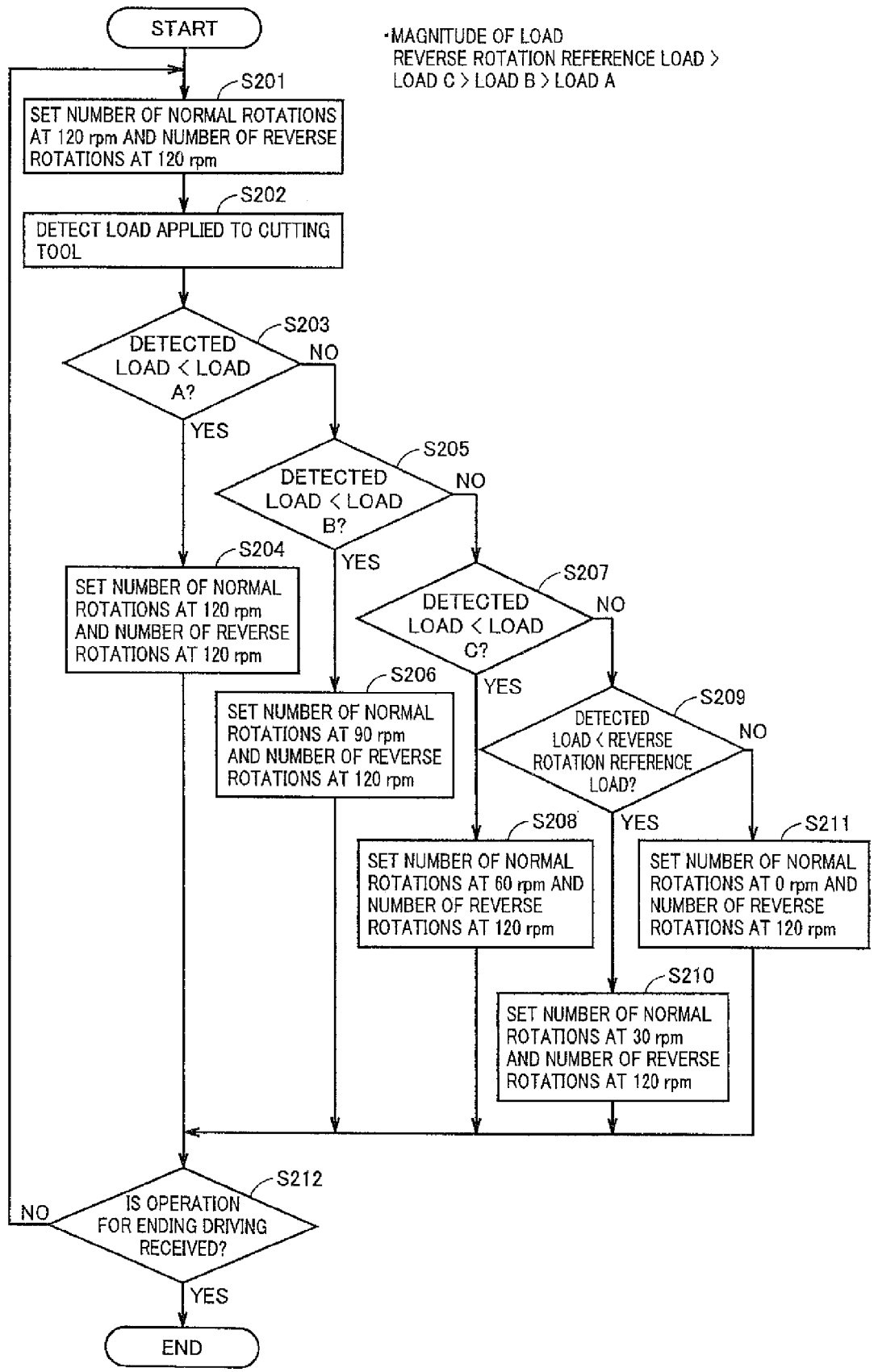
FIG. 11 is a flowchart for describing another example of driving of the cutting tool of the root canal treating device according to the third embodiment of the present invention.

FIG. 11 is a flowchart for describing another example of driving of cutting tool 5 of root canal treating device 100 according to the third embodiment of the present invention. First, controller 11 sets the number of normal rotations at 120 rpm and the number of reverse rotations at 120 rpm (initial values), and drives cutting tool 5 (step S201). The initial values (e.g., 160 degrees for the normal rotation angle and 40 degrees for the reverse rotation angle) set in controller 11 are used as the normal rotation angle and the reverse rotation angle, and they are not changed in the process in the flowchart shown in FIG. 11.

Next, resistor 13d for load detection detects the load applied to cutting tool 5 when cutting tool 5 is rotated in the reverse rotation direction by 40 degrees (predetermined reverse rotation angle) (step S202). The detection of the load applied to cutting tool 5 in step S202 is the same as the detection of the load applied to cutting tool 5 in step S102, and thus, detailed description will not be repeated.

Next, comparing circuit 110 compares the load detected by resistor 13d for load detection and load A set in setting unit 14 (step S203). If the detected load is smaller than load A (YES in step S203), controller 11 sets the number of normal rotations at 120 rpm and the number of reverse rotations at 120 rpm, and controls the driving of cutting tool 5 (step S204). Namely, controller 11 determines that the load applied to cutting tool 5 is not worth considering because the detected load is smaller than load A, and sets the number of normal rotations and the number of reverse rotations at the initial values and controls the driving of cutting tool 5. The comparison between the detected load and the reverse rotation reference load in step S203 is the same as the comparison between the detected load and the reverse rotation reference load in step S103, and thus, detailed description will not be repeated.

On the other hand, if the detected load is equal to or larger than load A (NO in step S203), comparing circuit 110 compares the load detected by resistor 13d for load detection and load B (>load A) set in setting unit 14 (step S205). If the detected load is smaller than load B (YES in step S205), controller 11 sets the number of normal rotations at 90 rpm and the number of reverse rotations at 120 rpm, and controls the driving of cutting tool 5 (step S206). Namely, since the small load is applied to cutting tool 5 though the detected load is smaller than load B, controller 11 sets the number of normal rotations to become smaller than the initial value in consideration of the load applied to cutting tool 5, and controls the driving of cutting tool 5.

On the other hand, if the detected load is equal to or larger than load B (NO in step S205), comparing circuit 110 compares the load detected by resistor 13d for load detection and load C (>load B) set in setting unit 14 (step S207). If the detected load is smaller than load C (YES in step S207), controller 11 sets the number of normal rotations at 60 rpm and the number of reverse rotations at 120 rpm, and controls the driving of cutting tool 5 (step S208). Namely, since the load equal to or larger than load B is applied to cutting tool 5 though the detected load is smaller than load C, controller 11 sets the number of normal rotations to become smaller than the value set in step S206, and controls the driving of cutting tool 5.

On the other hand, if the detected load is equal to or larger than load C (NO in step S207), comparing circuit 110 compares the load detected by resistor 13d for load detection and the reverse rotation reference load (>load C) set by variable resistor 14a for setting the reference load (reverse rotation reference load) in setting unit 14 (step S209). If the detected load is smaller than the reverse rotation reference load (YES in step S209), controller 11 sets the number of normal rotations at 30 rpm and the number of reverse rotations at 120 rpm, and controls the driving of cutting tool 5 (step S210). Namely, since the load equal to or larger than load C is applied to cutting tool 5 though the detected load is smaller than the reverse rotation reference load, controller 11 sets the number of normal rotations to become smaller than the value set in step S208, and controls the driving of cutting tool 5.

On the other hand, if the detected load is equal to or larger than the reverse rotation reference load (NO in step S209), controller 11 sets the number of normal rotations at 0 rpm and the number of reverse rotations at 120 rpm, and controls the driving of cutting tool 5 (step S211). Namely, controller 11 performs the driving for further rotating cutting tool 5 in the reverse rotation direction by 40 degrees without rotating cutting tool 5 in the normal rotation direction, similarly to the first embodiment.

Controller 11 controls the driving of cutting tool 5 in accordance with the numbers of normal rotations and the numbers of reverse rotations set in steps S204, S206, S208, S210, and S211, and thereafter, determines whether the operation for ending the driving is received from operation unit 15 or not (step S212). If the operation for ending the driving is received from operation unit 15 (YES in step S212), controller 11 ends the driving. If the operation for ending the driving is not received from operation unit 15 (NO in step S212), the process returns to step S202 and resistor 13d for load detection detects the load applied to cutting tool 5 when cutting tool 5 is rotated in the reverse rotation direction by 40 degrees.

Such an example of root canal treating device 100 has been described that in steps S201 to S211, the parameter of the number of normal rotations is gradually reduced and cutting tool 5 is driven, as the load applied to cutting tool 5 becomes larger in the order of load A, load B, load C, and the reverse rotation reference load. The present invention is not, however, limited thereto. In root canal treating device 100, the parameter of the number of normal rotations may be continuously changed in accordance with the load applied to cutting tool 5. For example, controller 11 continuously changes the parameter of the number of normal rotations from 120 rpm to 0 rpm in accordance with the change of the load applied to cutting tool 5 from load A to the reverse rotation reference load. Furthermore, in root canal treating device 100, the parameter of the number of reverse rotations may also be changed in accordance with the load applied to cutting tool 5. An upper limit value of each of the number of normal rotations and the number of reverse rotations is not limited to 120 rpm. The number of rotations may be set to be equal to or larger than 120 rpm and the reference load may be set in accordance with the number of rotations.

The flowchart shown in FIG. 10 describes the example in which controller 11 changes only the parameter of the rotation angle in accordance with the load applied to cutting tool 5, and the flowchart shown in FIG. 11 describes the example in which controller 11 changes only the parameter of the number of rotations in accordance with the load applied to cutting tool 5. Root canal treating device 100 according to the third embodiment is not, however, limited thereto. By combining the process shown in FIG. 10 and the process shown in FIG. 11, controller 11 may change both the parameter of the rotation angle and the parameter of the number of rotations in accordance with the load applied to cutting tool 5.

FIG. 12 is a diagram showing combinations of the parameters changed in accordance with the load applied to cutting tool 5. In setting 1 shown in FIG. 12 (in the case of the flowchart shown in FIG. 10), controller 11 sets only the normal rotation angle to become smaller, as the load applied to cutting tool 5 becomes larger. In setting 2 (in the case of the flowchart shown in FIG. 11), controller 11 sets only the number of normal rotations to become smaller, as the load applied to cutting tool 5 becomes larger. In setting 3, controller 11 sets the normal rotation angle and the number of normal rotations to become smaller, as the load applied to cutting tool 5 becomes larger.

In setting 4, controller 11 sets only the reverse rotation angle to become larger, as the load applied to cutting tool 5 becomes larger. In setting 5, controller 11 sets only the number of reverse rotations to become larger, as the load applied to cutting tool 5 becomes larger. In setting 6, controller 11 sets the reverse rotation angle and the number of reverse rotations to become larger, as the load applied to cutting tool 5 becomes larger.

In setting 7, controller 11 sets only the normal rotation angle to become smaller and sets only the reverse rotation angle to become larger, as the load applied to cutting tool 5 becomes larger. In setting 8, controller 11 sets only the normal rotation angle to become smaller and sets only the number of reverse rotations to become larger, as the load applied to cutting tool 5 becomes larger. In setting 9, controller 11 sets only the normal rotation angle to become smaller and sets the reverse rotation angle and the number of reverse rotations to become larger, as the load applied to cutting tool 5 becomes larger.

In setting 10, controller 11 sets only the number of normal rotations to become smaller and sets only the reverse rotation angle to become larger, as the load applied to cutting tool 5 becomes larger. In setting 11, controller 11 sets only the number of normal rotations to become smaller and sets only the number of reverse rotations to become larger, as the load applied to cutting tool 5 becomes larger. In setting 12, controller 11 sets only the number of normal rotations to become smaller and sets the reverse rotation angle and the number of reverse rotations to become larger, as the load applied to cutting tool 5 becomes larger.

In setting 13, controller 11 sets the normal rotation angle and the number of normal rotations to become smaller and sets only the reverse rotation angle to become larger, as the load applied to cutting tool 5 becomes larger. In setting 14, controller 11 sets the normal rotation angle and the number of normal rotations to become smaller and sets only the number of reverse rotations to become larger, as the load applied to cutting tool 5 becomes larger. In setting 15, controller 11 sets the normal rotation angle and the number of normal rotations to become smaller and sets the reverse rotation angle and the number of reverse rotations to become larger, as the load applied to cutting tool 5 becomes larger.

In the foregoing description, controller 11 changes at least one parameter of the normal rotation angle and the number of normal rotations as well as the reverse rotation angle and the number of reverse rotations such that at least one parameter of the normal rotation angle and the number of normal rotations becomes smaller or at least one parameter of the reverse rotation angle and the number of reverse rotations becomes larger as the load applied to cutting tool 5 becomes larger.

However, controller 11 may change at least one parameter of the normal rotation angle and the number of normal rotations as well as the reverse rotation angle and the number of reverse rotations such that the reverse rotation angle becomes larger than the normal rotation angle and/or the number of reverse rotations becomes larger than the number of normal rotations as the load applied to cutting tool 5 becomes larger. For example, controller 11 can change the parameters as in step S111 shown in FIG. 10 (normal rotation angle=0 degree, reverse rotation angle=40 degrees) and as in step S206 shown in FIG. 11 (number of normal rotations=90 rpm, number of reverse rotations=120 rpm), thereby reducing the load applied to cutting tool 5.

FIG. 13 is a diagram showing relation between the parameters changed in accordance with the load applied to cutting tool 5. In setting A shown in FIG. 13, controller 11 changes at least one parameter of the normal rotation angle and the reverse rotation angle such that the reverse rotation angle becomes larger than the normal rotation angle, as the load applied to cutting tool 5 becomes larger. For example, when controller 11 controls the driving of cutting tool 5 with the normal rotation angle being 60 degrees and the reverse rotation angle being 30 degrees, controller 11 may change the normal rotation angle to 20 degrees, or may change the reverse rotation angle to 70 degrees, or may change the normal rotation angle to 30 degrees and the reverse rotation angle to 70 degrees, as long as the reverse rotation angle becomes larger than the normal rotation angle.

In setting B, controller 11 changes at least one parameter of the number of normal rotations and the number of reverse rotations such that the number of reverse rotations becomes larger than the number of normal rotations, as the load applied to cutting tool 5 becomes larger. For example, when controller 11 controls the driving of cutting tool 5 with the number of normal rotations being 200 rpm and the number of reverse rotations being 100 rpm, controller 11 may change the number of normal rotations to 100 rpm, or may change the number of reverse rotations to 300 rpm, or may change the number of normal rotations to 100 rpm and the number of reverse rotations to 300 rpm, as long as the number of reverse rotations becomes larger than the number of normal rotations.

In setting C, controller 11 changes at least one parameter of the normal rotation angle and the reverse rotation angle as well as the number of normal rotations and the number of reverse rotations such that the reverse rotation angle becomes larger than the normal rotation angle and the number of reverse rotations becomes larger than the number of normal rotations, as the load applied to cutting tool 5 becomes larger. For example, when controller 11 controls the driving of cutting tool 5 with the normal rotation angle being 60 degrees, the reverse rotation angle being 30 degrees, the number of normal rotations being 200 rpm, and the number of reverse rotations being 100 rpm, controller 11 may change the normal rotation angle to 20 degrees and the number of normal rotations to 100 rpm, or may change the reverse rotation angle to 70 degrees and the number of reverse rotations to 300 rpm, or may change the normal rotation angle to 30 degrees, the reverse rotation angle to 70 degrees, the number of normal rotations to 100 rpm, and the number of reverse rotations to 300 rpm, as long as the reverse rotation angle becomes larger than the normal rotation angle and the number of reverse rotations becomes larger than the number of normal rotations.

As described above, in root canal treating device 100 according to the third embodiment of the present invention, at least one parameter of the normal rotation angle and the number of normal rotations as well as the reverse rotation angle and the number of reverse rotations is changed in accordance with the load applied to cutting tool 5 which is detected by resistor 13d for load detection. Therefore, in root canal treating device 100, the twist driving of cutting tool 5 can be performed with the reduced load applied to cutting tool 5. Therefore, breakage of the cutting tool due to the applied load can be prevented.

Fourth Embodiment

In a root canal treating device according to a fourth embodiment of the present invention, at least one parameter of the rotation angle and the rotation angular speed in the normal rotation as well as the rotation angle and the rotation angular speed in the reverse rotation is changed in accordance with a position of the tip end of the cutting tool in the root canal (hereinafter, also simply referred to as "detected position" or "position of the cutting tool") obtained by the root canal length measuring circuit.

Figure 14:
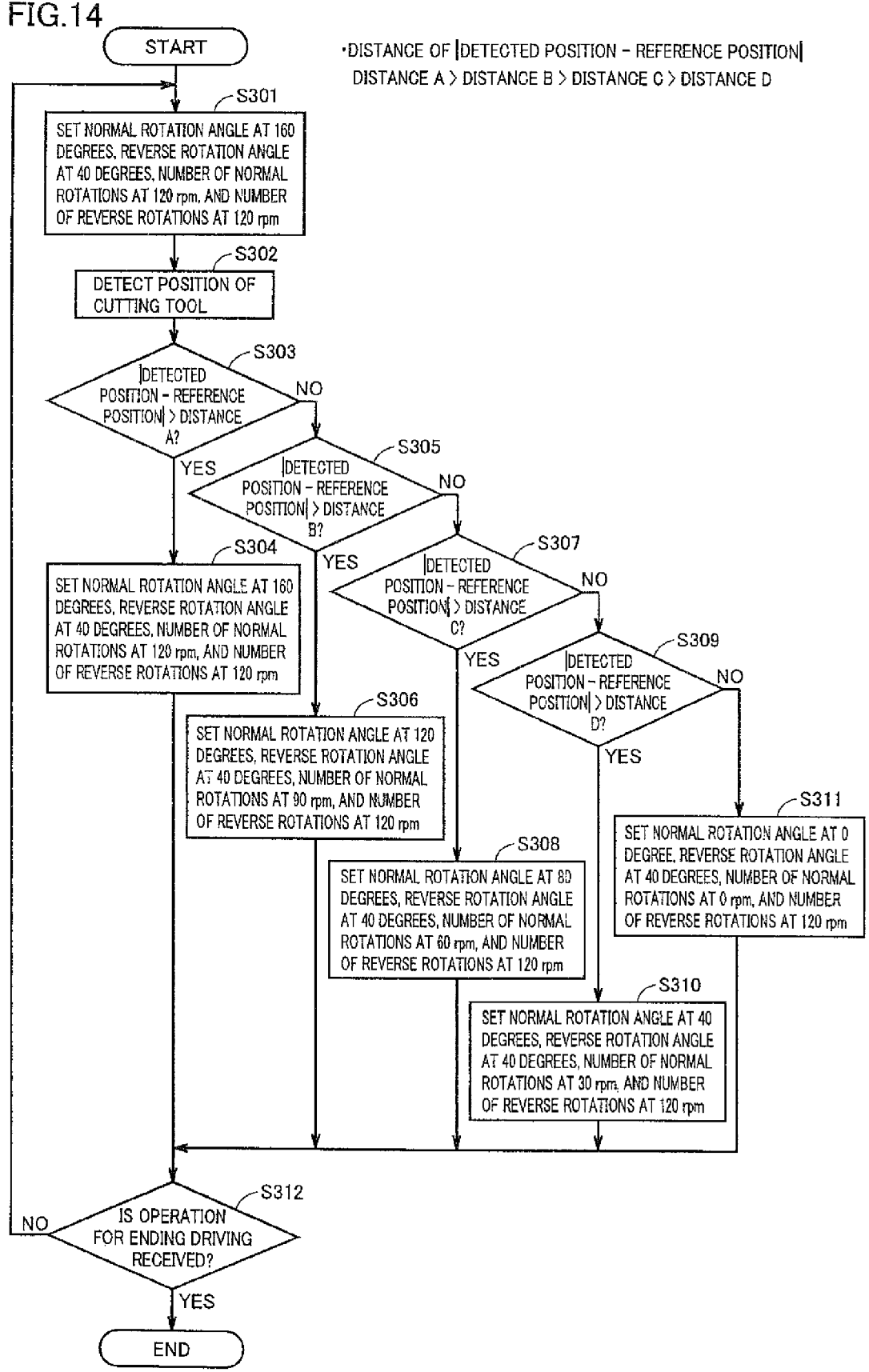
FIG. 14 is a flowchart for describing one example of driving of a cutting tool of a root canal treating device according to a fourth embodiment of the present invention.

FIG. 14 is a flowchart for describing one example of driving of cutting tool 5 of root canal treating device 100 according to the fourth embodiment of the present invention. Since the root canal treating device according to the fourth embodiment has the same configuration as that of root canal treating device 100 according to the first embodiment shown in FIGS. 1 to 3, the same reference characters are used and detailed description will not be repeated. In addition, in root canal treating device 100 according to the fourth embodiment, it is assumed that as cutting tool 5 comes closer to a reference position (e.g., a position of a root apex), a distance from the detected position to the reference position (|detected position−reference position|) changes in the order of a distance A, a distance B, a distance C, and a distance D (distance A>distance B>distance C>distance D).

First, controller 11 sets the normal rotation angle at 160 degrees, the reverse rotation angle at 40 degrees, the number of normal rotations at 120 rpm, and the number of reverse rotations at 120 rpm (initial values), and controls the driving of cutting tool 5 (step S301).

Next, root canal length measuring circuit 12 detects the position of cutting tool 5 after the driving in step S301 is performed (step S302). Comparing circuit 110 determines whether the distance from the detected position to the reference position is longer than distance A or not (step S303). If comparing circuit 110 determines that the distance from the position detected by root canal length measuring circuit 12 to the reference position is longer than distance A (YES in step S303), controller 11 sets the normal rotation angle at 160 degrees, the reverse rotation angle at 40 degrees, the number of normal rotations at 120 rpm, and the number of reverse rotations at 120 rpm (initial values), and controls the driving of cutting tool 5 (step S304). Namely, since the detected position of cutting tool 5 has not yet reached a position A, controller 11 maintains the setting at the initial values and controls the driving of cutting tool 5.

On the other hand, if comparing circuit 110 determines that the distance from the position detected by root canal length measuring circuit 12 to the reference position is equal to or shorter than distance A (NO in step S303), comparing circuit 110 determines whether the distance from the detected position to the reference position is longer than distance B or not (step S305). If comparing circuit 110 determines that the distance from the position detected by root canal length measuring circuit 12 to the reference position is longer than distance B (YES in step S305), controller 11 sets the normal rotation angle at 120 degrees, the reverse rotation angle at 40 degrees, the number of normal rotations at 90 rpm, and the number of reverse rotations at 120 rpm, and controls the driving of cutting tool 5 (step S306). Namely, since the detected position of cutting tool 5 has reached position A, controller 11 sets the normal rotation angle and the number of normal rotations to become smaller than the initial values in order to reduce the load applied to cutting tool 5, and controls the driving of cutting tool 5.

On the other hand, if comparing circuit 110 determines that the distance from the position detected by root canal length measuring circuit 12 to the reference position is equal to or shorter than distance B (NO in step S305), comparing circuit 110 determines whether the distance from the detected position to the reference position is longer than distance C or not (step S307). If comparing circuit 110 determines that the distance from the position detected by root canal length measuring circuit 12 to the reference position is longer than distance C (YES in step S307), controller 11 sets the normal rotation angle at 80 degrees, the reverse rotation angle at 40 degrees, the number of normal rotations at 60 rpm, and the number of reverse rotations at 120 rpm, and controls the driving of cutting tool 5 (step S308). Namely, since the detected position of cutting tool 5 has reached a position B, controller 11 sets the normal rotation angle and the number of normal rotations to become smaller than the initial values at position A in order to reduce the load applied to cutting tool 5, and controls the driving of cutting tool 5.

On the other hand, if comparing circuit 110 determines that the distance from the position detected by root canal length measuring circuit 12 to the reference position is equal to or shorter than distance C (NO in step S307), comparing circuit 110 determines whether the distance from the detected position to the reference position is longer than distance D or not (step S308). If comparing circuit 110 determines that the distance from the position detected by root canal length measuring circuit 12 to the reference position is longer than distance D (YES in step S309), controller 11 sets the normal rotation angle at 40 degrees, the reverse rotation angle at 40 degrees, the number of normal rotations at 30 rpm, and the number of reverse rotations at 120 rpm, and controls the driving of cutting tool 5 (step S310). Namely, since the detected position of cutting tool 5 has reached a position C, controller 11 sets the normal rotation angle and the number of normal rotations to become smaller than the initial values at position B in order to reduce the load applied to cutting tool 5, and controls the driving of cutting tool 5.

On the other hand, if comparing circuit 110 determines that the distance from the position detected by root canal length measuring circuit 12 to the reference position is equal to or shorter than distance D (NO in step S309), controller 11 sets the normal rotation angle at 0 degree, the reverse rotation angle at 40 degrees, the number of normal rotations at 0 rpm, and the number of reverse rotations at 120 rpm, and controls the driving of cutting tool 5 (step S310). Namely, since the detected position of cutting tool 5 has reached a position D and come closer to the reference position, controller 11 controls the driving of cutting tool 5 such that the rotation in the normal rotation direction is stopped and cutting tool 5 is rotated only in the reverse rotation direction.

Controller 11 controls the driving of cutting tool 5 in accordance with the normal rotation angles and the reverse rotation angles as well as the numbers of normal rotations and the numbers of reverse rotations set in steps S304, S306, S308, S310, and S311, and thereafter, determines whether the operation for ending the driving is received from operation unit 15 or not (step S312). If the operation for ending the driving is received from operation unit 15 (YES in step S312), controller 11 ends the driving. If the operation for ending the driving is not received from operation unit 15 (NO in step S312), the process returns to step S302 and root canal length measuring circuit 12 detects the position of cutting tool 5 after the driving in step S301 is performed.

Such an example of root canal treating device 100 has been described that in steps S301 to S311, the parameters of the normal rotation angle and the number of normal rotations are gradually reduced and cutting tool 5 is driven as the position of cutting tool 5 comes closer to the reference position in the order of distance A, distance B, distance C, and distance D. The present invention is not, however, limited thereto. In root canal treating device 100, the parameters of the normal rotation angle and the number of normal rotations may be continuously changed in accordance with the position of cutting tool 5. For example, controller 11 continuously changes the parameter of the normal rotation angle from 160 degrees to 0 degree and the parameter of the number of normal rotations from 120 rpm to 0 rpm in accordance with the change of the position of cutting tool 5 from distance A to distance D. Furthermore, in root canal treating device 100, the parameters of the reverse rotation angle and the number of reverse rotations may also be changed in accordance with the position of cutting tool 5. At this time, the predetermined reverse rotation angle, which is a timing at which resistor 13*d* for load detection detects the load applied to cutting tool 5, is also changed in accordance with the change of the parameter of the reverse rotation angle. An upper limit value of each of the normal rotation angle and the reverse rotation angle is not limited to 160 degrees. The rotation angle may be set to be equal to or larger than 160 degrees and the reference position may be set in accordance with the rotation angle. Furthermore, an upper limit value of each of the number of normal rotations and the number of reverse rotations is not limited to 120 rpm. The number of rotations may be set to be equal to or larger than 120 rpm and the reference position may be set in accordance with the number of rotations.

As described above, in root canal treating device 100 according to the fourth embodiment, at least one parameter of the rotation angle and the rotation angular speed in the normal rotation as well as the rotation angle and the rotation angular speed in the reverse rotation is changed in accordance with the position of the cutting tool. Therefore, the load applied to cutting tool 5 can be controlled to fall within an appropriate range, and breakage of cutting tool 5 and excessive cutting by cutting tool 5 can be prevented.

Root canal treating device 100 according to the fourth embodiment can be combined with root canal treating devices 100 according to the first to third embodiments. For example, by combining root canal treating device 100 according to the fourth embodiment with root canal treating device 100 according to the first embodiment, after cutting tool 5 is rotated in the reverse rotation direction by 40 degrees, the next rotation direction may be determined in accordance with whether or not the detected load is equal to or larger than the reference load, and the parameters of the rotation angle and the rotation angular speed in the next rotation may be changed in accordance with the position of the cutting tool. By combining root canal treating device 100 according to the fourth embodiment with root canal treating device 100 according to the third embodiment, the parameters such as the rotation angle may be changed based on the load applied to cutting tool 5, and the parameters such as the rotation angle may be changed in accordance with the position of the cutting tool.

Figure 15:
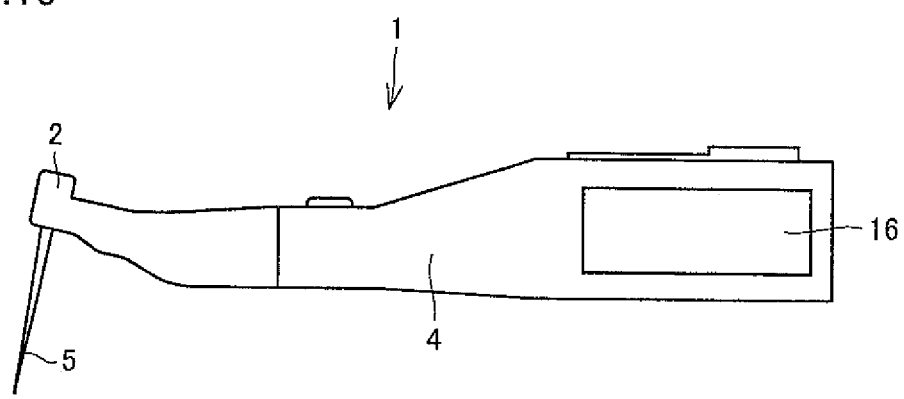
FIG. 15 is a schematic diagram showing a configuration of a cordless-type root canal treating device.

Furthermore, in root canal treating devices 100 according to the first to fourth embodiments, the configuration in which hand piece 1 is coupled to control box 9 via hose 61 has been described. The present invention is not, however, limited thereto but may be configured as a cordless-type root canal treating device. FIG. 15 is a schematic diagram showing a configuration of the cordless-type root canal treating device. In the cordless-type root canal treating device shown in FIG. 15, a battery pack, a micro motor, and a control system corresponding to a control box are incorporated into grip 4 of hand piece 1, and each type of operation units is disposed on a surface of grip 4. Furthermore, in the cordless-type root canal treating device, grip 4 is provided with display unit 16. Therefore, without significantly changing a user's line of sight, the user can check information such as whether cutting tool 5 is being driven in normal rotation driving or in reverse rotation driving, where the current position of cutting tool 5 is, how much load is being applied to cutting tool 5, and what is the number of rotations. Although not shown, lead 19 for mouth electrode 19*a* may be configured to be led from grip 4.

In addition, in root canal treating devices 100 according to the first to fourth embodiments, the case where micro motor 7 is used as a power source for driving cutting tool 5 has been described. The present invention is not, however, limited thereto. Another driving source such as an air turbine may be used.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A dental treating apparatus, comprising:
a hand piece for drivably holding a cutting tool on a head unit;
a driving unit for driving said cutting tool, assuming that a normal rotation is a rotation in a direction in which said cutting tool cuts an object to be cut and a reverse rotation is a rotation in an opposite direction of said normal rotation;
a load detecting unit for detecting a load applied to said cutting tool;
a load comparing unit for comparing the load detected by said load detecting unit and a reverse rotation reference load; and
a control unit for controlling said driving unit based on a result of comparison by said load comparing unit, each time said driving unit performs driving for rotating said cutting tool in said reverse rotation direction,
wherein each time said driving unit performs driving for rotating said cutting tool in said reverse rotation direction by a predetermined reverse rotation angle, said control unit controls said driving unit based on the result of comparison by said load comparing unit.

2. The dental treating apparatus according to claim 1, wherein when the result of comparison by said load comparing unit attains a predetermined result, said control unit further drives said cutting tool in said reverse rotation direction.

3. The dental treating apparatus according to claim 2, wherein said predetermined result is a case in which the load detected by said load detecting unit becomes equal to or larger than said reverse rotation reference load.

4. The dental treating apparatus according to claim 1, wherein each time said driving unit performs driving for rotating said cutting tool in a normal rotation direction by a predetermined normal rotation angle, said control unit executes control to perform driving for rotating said cutting tool in said reverse rotation direction, when the load detected by said load detecting unit becomes equal to or larger than a normal rotation reference load.

5. The dental treating apparatus according to claim 4, wherein said normal rotation reference load is larger than said reverse rotation reference load.

6. The dental treating apparatus according to claim 4, wherein said predetermined normal rotation angle is larger than said predetermined reverse rotation angle.

7. The dental treating apparatus according to claim 1, wherein said control unit changes at least one parameter of a rotation angle and a rotation angular speed in the normal rotation as well as a rotation angle and a rotation angular speed in the reverse rotation, in accordance with the result of comparison by said load comparing unit.

8. The dental treating apparatus according to claim 7, wherein said control unit changes at least one parameter of the rotation angle and the rotation angular speed in the normal rotation as well as the rotation angle and the rotation angular speed in the reverse rotation such that at least one parameter of the rotation angle and the rotation angular speed in the normal rotation becomes smaller or at least one parameter of the rotation angle and the rotation angular speed in the reverse rotation becomes larger as the load detected by said load detecting unit becomes larger than said reverse rotation reference load as a result of comparison by said load comparing unit.

9. The dental treating apparatus according to claim 7, wherein said control unit changes at least one parameter of the rotation angle and the rotation angular speed in the normal rotation as well as the rotation angle and the rotation angular speed in the reverse rotation such that the rotation angle in the reverse rotation becomes larger than the rotation angle in the normal rotation and/or the rotation angular speed in the reverse rotation becomes larger than the rotation angular speed in the normal rotation as the load detected by said load detecting unit becomes larger than said reverse rotation reference load as a result of comparison by said load comparing unit.

10. The dental treating apparatus according to claim 1, wherein by using a value of the load detected by said load detecting unit during rotation of said cutting tool by said predetermined reverse rotation angle, said load comparing unit compares the load detected by said load detecting unit and said reverse rotation reference load.

11. The dental treating apparatus according to claim 10, wherein said load comparing unit uses a maximum value, an average value or at least one of a plurality of values of the load detected by said load detecting unit during rotation of said cutting tool by said predetermined reverse rotation angle.

12. The dental treating apparatus according to claim 1, wherein said driving unit sets a reverse rotation angular speed when said cutting tool is driven in said reverse rotation direction to be higher than a rotation angular speed when said cutting tool is driven in said normal rotation direction.

13. The dental treating apparatus according to claim 1, further comprising a driving state detecting unit for detecting a position of a tip end of said cutting tool in a root canal obtained by electrical root canal length measurement, wherein said control unit changes said reverse rotation reference load in accordance with said position detected by said driving state detecting unit.

14. The dental treating apparatus according to claim 13, wherein said control unit changes said reverse rotation reference load to become smaller as said position detected by said driving state detecting unit comes closer to a predetermined reference position.

15. The dental treating apparatus according to claim 4, further comprising a driving state detecting unit for detecting a position of a tip end of said cutting tool in a root canal obtained by electrical root canal length measurement, wherein said control unit changes at least one of said predetermined normal rotation angle and said predetermined reverse rotation angle in accordance with said position detected by said driving state detecting unit.

16. The dental treating apparatus according to claim 15, wherein said control unit changes at least one of said predetermined normal rotation angle and said predetermined reverse rotation angle to become smaller as said position detected by said driving state detecting unit comes closer to a predetermined reference position.

17. The dental treating apparatus according to claim 1, further comprising a notifier for notifying a user of whether said cutting tool is being driven in said normal rotation direction or in said reverse rotation direction.

18. The dental treating apparatus according to claim 17, wherein said notifier is a display unit and is provided at said hand piece.

* * * * *